(12) United States Patent
O'Mahony et al.

(10) Patent No.: US 7,955,289 B2
(45) Date of Patent: *Jun. 7, 2011

(54) METHOD AND APPARATUS FOR BLOOD WITHDRAWAL AND INFUSION USING A PRESSURE CONTROLLER

(75) Inventors: John O'Mahony, Maple Grove, MN (US); Mark Gelfand, New York, NY (US); Edward G. Rychlick, Osseo, MN (US)

(73) Assignee: CHF Solutions, Inc., New York, NY (US)

( * ) Notice: Subject to any disclaimer, the term of this patent is extended or adjusted under 35 U.S.C. 154(b) by 121 days.

This patent is subject to a terminal disclaimer.

(21) Appl. No.: 12/330,171

(22) Filed: Dec. 8, 2008

(65) Prior Publication Data

US 2009/0149795 A1    Jun. 11, 2009

Related U.S. Application Data

(60) Division of application No. 11/154,569, filed on Jun. 17, 2005, now Pat. No. 7,462,161, which is a continuation of application No. 10/601,574, filed on Jun. 24, 2003, now Pat. No. 7,674,237, which is a continuation of application No. 09/703,702, filed on Nov. 2, 2000, now Pat. No. 6,585,675.

(51) Int. Cl.
*A61M 37/00* (2006.01)
(52) U.S. Cl. ........... 604/4.01; 604/6.11; 604/65; 604/67
(58) Field of Classification Search .................. 604/4.01, 604/5.01, 5.04, 6.1, 6.09, 6.11, 6.06, 65–67, 604/7, 6.14; 210/645, 646, 739, 741, 90, 210/600, 650, 651, 634, 192.2, 200, 252, 210/257.2, 258, 416.1, 321.71, 433.1, 500.21; 422/44, 45, 48

See application file for complete search history.

(56) References Cited

U.S. PATENT DOCUMENTS

| 3,648,694 | A | 3/1972 | Mogos et al. |
| 3,756,234 | A | 9/1973 | Kopp |
| 4,080,958 | A | 3/1978 | Bregman et al. |
| 4,086,924 | A | 5/1978 | Latham, Jr. |

(Continued)

FOREIGN PATENT DOCUMENTS

| DE | 26 44 062 | 9/1976 |
| EP | 0 274 178 | 7/1988 |
| EP | 0 990 444 A2 | 4/2000 |
| GB | 1 583 023 | 1/1981 |
| WO | WO 97/15228 | 5/1997 |

OTHER PUBLICATIONS

Strife, C.F. et al, "Experience With a Low Volume Ultrafiltration Cell in Small Children," Clinical Nephrology 8:410-413 (1977).

(Continued)

*Primary Examiner* — Leslie R Deak
(74) *Attorney, Agent, or Firm* — Nixon & Vanderhye P.C.

(57) ABSTRACT

A method and apparatus for controlling blood withdrawal and infusion flow rate with the use of a pressure controller. The pressure controller uses pressure targets based upon occlusion limits that are calculated as a function of flow. The controller has the ability to switch from controlling withdrawal pressure to controlling infusion pressure based upon the detection of an occlusion. The controller distinguishes between partial and total occlusions of the withdrawal vein providing blood access. Depending on the nature of occlusion, the controller limits or temporarily reverses blood flow and, thus, prevents withdrawal vessel collapse or reverses blood flow to quickly infuse blood into the vessel without participation from operator.

25 Claims, 9 Drawing Sheets

U.S. PATENT DOCUMENTS

| | | | |
|---|---|---|---|
| 4,498,983 | A | 2/1985 | Bilstad et al. |
| 4,657,529 | A | 4/1987 | Prince et al. |
| 4,784,768 | A | 11/1988 | Mathieu |
| 4,936,980 | A | 6/1990 | Yoshimichi et al. |
| 5,098,373 | A | 3/1992 | Polaschegg |
| 5,114,580 | A | 5/1992 | Ahmad et al. |
| 5,178,603 | A * | 1/1993 | Prince .................... 604/6.01 |
| 5,188,588 | A | 2/1993 | Schoendorfer et al. |
| 5,312,550 | A | 5/1994 | Hester |
| 5,366,630 | A | 11/1994 | Chevallet |
| 5,392,653 | A | 2/1995 | Zanger |
| 5,454,374 | A | 10/1995 | Omachi |
| 5,476,451 | A | 12/1995 | Ensminger et al. |
| 5,536,237 | A | 7/1996 | Prince et al. |
| 5,595,943 | A | 1/1997 | Itabashi et al. |
| 5,685,989 | A | 11/1997 | Krivitski et al. |
| 5,707,086 | A | 1/1998 | Treu et al. |
| 5,725,776 | A | 3/1998 | Kenley et al. |
| 5,730,712 | A | 3/1998 | Falkvall et al. |
| 5,894,011 | A | 4/1999 | Prosl et al. |
| 5,906,589 | A | 5/1999 | Gordon et al. |
| 5,910,252 | A | 6/1999 | Truitt et al. |
| 6,077,443 | A | 6/2000 | Goldau |
| 6,090,048 | A | 7/2000 | Hertz et al. |
| 6,146,523 | A | 11/2000 | Kenley et al. |
| 6,177,049 | B1 | 1/2001 | Schnell et al. |
| 6,200,485 | B1 * | 3/2001 | Kitaevich et al. .............. 210/739 |
| 6,308,737 | B1 | 10/2001 | Krivitski |
| 6,423,022 | B1 | 7/2002 | Roeher et al. |
| 6,579,241 | B2 | 6/2003 | Roeher |
| 6,585,675 | B1 * | 7/2003 | O'Mahony et al. .......... 604/4.01 |
| 6,595,942 | B2 | 7/2003 | Kleinekofort |
| 6,623,443 | B1 | 9/2003 | Polaschegg |
| 6,673,314 | B1 | 1/2004 | Burbank et al. |
| 6,676,621 | B1 | 1/2004 | Menninger |
| 6,691,047 | B1 | 2/2004 | Fredericks |
| 6,767,333 | B1 | 7/2004 | Müller et al. |
| 6,775,577 | B2 | 8/2004 | Crnkovich et al. |
| 6,780,322 | B1 | 8/2004 | Bissler et al. |
| 6,796,955 | B2 | 9/2004 | O'Mahony |
| 2001/0016699 | A1 | 8/2001 | Burbank et al. |
| 2001/0021817 | A1 | 9/2001 | Brugger et al. |
| 2001/0037079 | A1 | 11/2001 | Burbank et al. |
| 2001/0041892 | A1 | 11/2001 | Burbank et al. |
| 2002/0068015 | A1 | 6/2002 | Polaschegg et al. |
| 2002/0103453 | A1 | 8/2002 | Burbank et al. |
| 2002/0147423 | A1 | 10/2002 | Burbank et al. |
| 2003/0009123 | A1 | 1/2003 | Brugger et al. |
| 2003/0097087 | A1 | 5/2003 | Gura |

OTHER PUBLICATIONS

Lauer, A. et al, "Continuous Arteriovenous Hemofiltration in the Critically Ill Patient, Clinical Use and Operational Characteristics," Annals of Internal Medicine 99:455-460 (1983).

Verbanck, J. et al, "Pure Ultrafiltration by Repeated Puncture of a Peripheral Arm-Vein as Treatment of Refratory Edema", The International Journal of Artificial Organs, vol. 3, No. 6 (1980), pp. 342-343.

Silverstein et al, "Treatment of Severe Fluid Overload by Ultrafiltration," The New England Journal of Medicine, vol. 291, No. 15, Oct. 10, 1974, pp. 747-751.

Blake, P. et al, "Refractory Congestive Heart Failure: Overview and Application of Extracorporeal Ultrafiltration," Critical Care Nephrology, *Advances in Renal Replacement Therapy*, vol. 3, No. 2 (Apr. 1966), pp. 166-173.

Civati G. et al, "Haemofiltration Without Substitution Fluid," Proc. EDTA-ERA, vol. 21 (1984), pp. 441-446.

Jenkins, R.D. et al, "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function by Dialysis, $4^{th}$ Ed., (1996) pp. 391-397.

Gupta, B.B. et al, "High Shear Rate Hemofiltration: Influence of Fiber Dimensions and Shear Rates," Artificial Organs, International Society for Artificial Organs, vol. 13(2) (1989), pp. 97-102.

Rimondini, A. et al, "Hemofiltration as Short-Term Treatment for Refractory Congestive Heart Failure," The American Journal of Medicine, vol. 83, Jul. 1987, pp. 43-48.

Donato, L. et al, "Treatment of End-Stage Congestive Heart Failure by Extracorporeal Ultrafiltration," The American Journal of Cardiology, vol. 59, (Feb. 1, 1987), pp. 379 and 380.

L'Abbate, A. et al, "Ultrafiltration: A Rational Treatment for Heart Failure," Cardiology 1989; 76:384-390.

Chen, Y. et al, "Direct Peripheral Venopuncture: Another New Choice of Temporary Vascular Access", Renal Failure, 22(3), 369-377 (2000).

International Search Report dated Jul. 9, 2002.

Piergiuseppe Agostoni et al., "Sustained Improvement in Functional Capacity After Removal of Body Fluid With Isolated Ultrafiltration in Chronic Cardiac Insufficiency: Failure of Furosemide to Provide the Same Result", Mar. 1994, The American Journal of Medicine, vol. 96, pp. 191-199.

Daniel Goldstein et al., "Venoarterial Shunting for the Treatment of Right Sided Circulatory Failure After Left Ventricular Assist Device Placement", ASAIO Journal 1997, pp. 171-176.

James Cimino et al., "Simple Venipuncture for Hemodialysis", The New England Journal of Medicine, Sep. 20, 1962, pp. 608-609.

Drukker et al., "Replacement of Renal Function by Dialysis", pp. 334-379.

International Search Report dated Sep. 11, 2002.

Jonathan D. Sackner-Bernstein, MD et al., "How Should Diuretic-Refractory, Volume-Overloaded Heart Failure Patients Be Managed?" The Journal of Invasive Cardiology, vol. 15, No. 10 (Oct. 2003), pp. 585-590.

Brian E. Jaski, MD et al., "Peripherally Inserted Veno-Venous Ultrafiltration for Rapid Treatment of Volume Overloaded Patients", Journal of Cardiac Failure, vol. 9, No. 3, (Jun. 2003), pp. 227-231.

* cited by examiner

METHOD AND APPARATUS FOR BLOOD WITHDRAWAL AND INFUSION USING A PRESSURE CONTROLLER

RELATED APPLICATIONS

This is a divisional application of U.S. patent application Ser. No. 11/154,569 (U.S. Pat. No. 7,462,161) filed Jun. 17, 2005 which is a continuation application of application Ser. No. 10/601,574 filed Jun. 24, 2003 which is a divisional application of U.S. patent application Ser. No. 09/703,702 (now U.S. Pat. No. 6,585,675) filed on Nov. 2, 2000, the entirety of all applications are incorporated by reference herein.

FIELD OF INVENTION

The invention relates to the field of pressure controllers for fluidic pumping systems and, in particular, to pressure controllers for intravenous blood pumps.

BACKGROUND OF THE INVENTION

There are a number of medical treatments, such as ultrafiltration, apheresis and dialysis, that require blood to be temporarily withdrawn from a patient and returned to the body shortly thereafter. While the blood is temporarily outside of the body, it flows through an "extracorporeal blood circuit" of tubes, filters, pumps and/or other medical components. In some treatments, the blood flow is propelled by the patient's blood pressure and gravity, and no artificial pump is required. In other treatments, blood pumps in the extracorporeal circuit provide additional force to move the blood through the circuit and to control the flow rate of blood through the circuit. These pumps may be peristaltic or roller pumps, which are easy to sterilize, are known to cause minimal clotting and damage to the blood cells, and are inexpensive and reliable.

Brushed and brushless DC motors are commonly used to rotate peristaltic pumps. A motor controller regulates the rotational speed of blood pumps. The speed of a pump, expressed as rotations per minute (RPM), regulates the flow rate of the blood through the circuit. Each revolution of the pump moves a known volume of blood through the circuit. Thus, the blood flow rate through the circuit can be easily derived from the pump speed. Accordingly, the pump speed provides a relatively accurate indicator for the volume flow of blood through an extracorporeal circuit.

Existing pump controllers may be as simple as a potentiometer that regulates the voltage to the pump DC motor. The pump speed is proportional to the voltage applied to the pump motor. By increasing the voltage, the speed of the pump increases and, similarly, the blood flow increases through the extracorporeal circuit. More sophisticated existing pump controllers, such as used in current dialysis machines, include a microprocessor that executes a software/firmware program to regulate the pump speed and, thus, blood flow in accordance with pump/flow settings entered by an operator. In these controllers, the microprocessor receives input commands from an operator who selects a desired blood flow using a user interface on the controller housing. The microprocessor determines the pump motor speed needed to provide the selected blood flow rate, and then issues commands to the pump motor to run at the proper speed.

To improve the accuracy and reliability of the blood flow through an extracorporeal circuit, existing pump controller microprocessors receive feedback signals from, for example, tachometers or optical encoders that sense the actual speed of the pump motor. Similarly, feedback signals have been provided by ultrasonic flow probes that measure the actual flow of blood in the extracorporeal circuit. By comparing the desired pump speed or flow rate to the measured pump speed or flow rate, the microprocessor can properly adjust the pump speed to correct for any difference between the desired and actual speed or rate. In addition, a calculated or measured flow value (actual flow rate) may be displayed on the pump console for viewing by the operator for a visual comparison with the desired flow setting.

The microprocessor controllers for blood pumps have, in the past, relied on both open and closed loop control of the motor speed. The open loop control normally consists of a constant feed forward voltage (based on the back EMF constant of the motor). The closed loop control systems use velocity feedback in the form of a tachometer, encoder or resolver to maintain constant pump flow. A constant flow control loop allows a user to set the blood flow rate, and the controller regulates the pump speed to maintain a constant blood flow, unless a malfunction occurs that would require the pump to be shut-down to protect the patient. The open loop control systems have the disadvantage that an increase or decrease in torque or motor resistance due to temperature will result in some variation in pump flow. This variation will generally be small when the motor is geared. Torque variations are not an issue for closed loop control systems because they use the motor velocity as feedback and adjust the supply current or voltage to the motor in order to maintain constant velocity.

Existing blood pump controllers include various alarms and interlocks that are set by a nurse or a medical technician (collectively referred to as the operator), and are intended to protect the patient. In a typical dialysis apparatus, the blood withdrawal and blood return pressures are measured in real time, so that sudden pressure changes are quickly detected. Sudden pressure changes in the blood circuit are treated as indicating an occlusion or a disconnect in the circuit. The detection of a sudden pressure change causes the controller to stop the pump and cease withdrawal of blood. The nurse or operator sets the alarm limits for the real time pressure measurements well beyond the expected normal operating pressure for the selected blood flow, but within a safe pressure operating range.

Examples of existing blood pump controllers are disclosed in U.S. Pat. Nos. 5,536,237 ('237 Patent) and 4,657,529 ('529 Patent). The controllers disclosed in these patents purport to optimize the rate of blood flow through a blood circuit based on a pressure vs. flow rate control curve. However, these patents do not teach controlling a blood pump based on control curves for both withdrawal and infusion pressures, and do not suggest reversing blood flow to relieve an occlusion. The authors of the '237 and '529 Patents acknowledged that during blood withdrawal, treatment is often interrupted if the vein is collapsed. They further acknowledged that as the result of such collapse the needle could be drawn into the blood vessel wall that makes the recovery difficult. The remedy proposed by these authors is to always withdraw blood at a rate that prevents the collapse of the vein by applying a complex system of identification of the vein capacity prior to treatment. The '237 Patent specifically addresses the difficulty of generating ad-hoc pressure flow relationships for individual patients with low venous flow capacity. However, the experience of the present applicants is that the withdrawal properties of venous access in many patients are prone to frequent and often abrupt changes during treatment. Accordingly, the approach advanced in the '237 and '529 Patents of attempting to always avoid vein collapse will fail when a vein collapse condition occurs and does not provide any remedy for vein collapse (other than to terminate treatment and call a nurse or doctor).

Pressure conditions in a blood circuit often change because of blood viscosity changes (that in turn affect flow resistance), and because of small blood clots that form where blood stagnates on the surface of tubes and cannulae. These small clots partially occlude the blood circuit, but do not totally obstruct blood flow through the circuit. These clot restrictions increase the flow resistance and, thus, increase the magnitude of pressure in the circuit. Accordingly, an assumption that the flow resistance and pressure are constants in a blood circuit may not be valid. Gravity is another source of pressure change in a blood circuit. Gravity affects the pressure in a blood circuit. The pressure in the circuit will change due to gravity if the patient moves such that the height changes occur with respect to the vertical position of the circuit entry and exit points on the patient's arms relative to the pressure sensors. The pressure sensors in the blood circuit may detect a change that is indicative of a change in the patient's position, rather than a clot in the circuit. For example, if the patient sits up, pressure sensors will detect pressure changes of the blood in the circuit.

If the gravity induced pressure changes are sufficiently large, prior pump controllers tended to activate an alarm and shut down the blood pump. The operator then has to respond to the alarm, analyze the situation and remedy the malfunction or change the alarm limits if the flow path conditions have changed. In more advanced systems the operator sets the alarm window size (for example, plus or minus 50 mmHg about a mean point), and the machine will automatically adjust the mean point in proportion to the flow setting change. If the measured pressure exceeds the pressure range set by the window, the blood flow is automatically stopped. However, existing systems do not adjust the pump speed in response to changes in flow resistance, but rather, shut down if the resistance (and hence fluid pressure) become excessive.

SUMMARY OF INVENTION

A blood flow controller has been developed that controls blood flow through an extracorporeal blood circuit. The controller regulates the flow rate through the circuit such that: (a) blood is withdrawn from a peripheral vein in the patient (which veins are usually small, collapsible tubes) at a blood flow rate sustainable by the vein and which avoids collapsing the vein, and (b) blood pressure changes in the circuit are compensated for by adjusting pump speed and hence the flow rate through the circuit. The controller sets a flow rate of blood through the circuit based on both a maximum flow rate limit and a variable limit of pressure vs. flow rate. These limits may be preprogrammed in the controller and/or selected by an operator.

A novel blood withdrawal system has been developed that enables rapid and safe recovery from occlusions in a withdrawal vein without participation of an operator, loss of circuits to clotting, or annoying alarms. Applicants have developed a technique of compensating for and remedying temporary vein collapse when it occurs during blood withdrawal. They recognized that not all episodes of a vein collapse require intervention from a doctor or nurse, and do not require that blood withdrawal ceased for an extended period. For example, vein collapse can temporarily occur when the patient moves or a venous spasm causes the vein to collapse in a manner that is too rapid to anticipate and temporary. There has been a long-felt need for a control system for an extracorporeal circuit that can automatically recover from temporary occlusions. Applicants developed a system that temporarily stops blood withdrawal when vein collapse occurs and, in certain circumstances, infuses blood into the collapsed vein to reopen the collapsed vein. Applicants' approach to vein collapse is counterintuitive and contrary to the approach disclosed in the '237 and '529 Patents.

Peripheral vein access presents unique problems that make it difficult for a blood withdrawal controller to maintain constant flow and not to create hazards for the patient. These problems are unlike those encountered with conventional dialysis treatments that rely on a surgically created arteriovenous shunt or fistula to withdraw blood and are administered in controlled dialysis centers. Using the present controller, for example, a patient may stand up during treatment and thereby increase the static pressure head height on the infusion side resulting in a false occlusion. The controller adjusts the blood flow rate through the extracorporeal circuit to accommodate for pressure changes. As the patient rises each centimeter (cm), the measured pressure in the extracorporeal circuit may increase by 0.73 mm Hg (milliliter of mercury). A change in height of 30 cm (approximately 1 ft) will result in a pressure change of 21 mm Hg. In addition, the patient may bend his/her arm during treatment and, thereby, reduce the blood flow to the withdrawal vein. As the flow through the withdrawal catheter decreases, the controller reduces pump speed to reduce the withdrawal pressure level. Moreover, the blood infusion side of the blood circulation circuit may involve similar pressure variances. These infusion side pressure changes are also monitored by the controller which may adjust the pump to accommodate such changes.

The controller may be incorporated into a blood withdrawal and infusion pressure control system which optimizes blood flow at or below a preset rate in accordance with a controller algorithm that is determined for each particular make or model of an extraction and infusion extracorporeal blood system. The controller is further a blood flow control system that uses real time pressure as a feedback signal that is applied to control the withdrawal and infusion pressures within flow rate and pressure limits that are determined in real time as a function of the flow withdrawn from peripheral vein access.

The controller may govern the pump speed based on control algorithms and in response to pressure signals from pressure sensors that detect pressures in the blood flow at various locations in the extracorporeal circuit. One example of a control algorithm is a linear relationship between a minimum withdrawal pressure and withdrawal blood flow. Another possible control algorithm is a maximum withdrawal flow rate. Similarly, a control algorithm may be specified for the infusion pressure of the blood returned to the patient. In operation, the controller seeks a maximum blood flow rate that satisfies the control algorithms by monitoring the blood pressure in the withdrawal tube (and optionally in the infusion tube) of the blood circuit, and by controlling the flow rate with a variable pump speed. The controller uses the highest anticipated resistance for the circuit and therefore does not adjust flow until this resistance has been exceeded. If the maximum flow rate results in a pressure level outside of the pressure limit for the existing flow rate, the controller responds by reducing the flow rate, such as by reducing the speed of a roller pump, until the pressure in the circuit is no greater than the minimum (or maximum for infusion) variable pressure limit. The controller automatically adjusts the pump speed to regulate the flow rate and the pressure in the circuit. In this manner, the controller maintains the blood pressure in the circuit within both the flow rate limit and the variable pressure limits that have been preprogrammed or entered in the controller.

In normal operation, the controller causes the pump to drive the blood through the extracorporeal circuit at a set maximum flow rate. In addition, the controller monitors the pressure to ensure that it conforms to the programmed variable pressure vs. flow limit. Each pressure vs. flow limit prescribes a minimum (or maximum) pressure in the withdrawal tube (or infusion tube) as a function of blood flow rate. If the blood pressure falls or rises beyond the pressure limit for a current flow rate, the controller adjusts the blood flow by reducing the pump speed. With the reduced blood flow, the pressure should rise in the withdrawal tube (or fall in the return infusion tube). The controller may continue to reduce the pump speed, until the pressure conforms to the pressure limit for the then current flow rate.

When the pressure of the adjusted blood flow, e.g. a reduced flow, is no less than (or no greater than) the pressure limit for that new flow rate (as determined by the variable pressure vs. flow condition), the controller maintains the pump speed and operation of the blood circuit at a constant rate. The controller may gradually advance the flow rate in response to an improved access condition, provided that the circuit remains in compliance with the maximum rate and the pressure vs. flow limit.

The controller has several advantages over the prior art including (without limitation): that the controller adjusts the pump speed to regulate the blood flow rate and maintain the blood pressure within prescribed limits, without requiring the attention of or adjustment by an operator; the controller adjusts blood flow in accordance with an occlusion pressure limit that varies with flow rate, and the controller adaptively responds to partial occlusions in the withdrawal blood flow. In addition, the controller implements other safety features, such as to detect the occurrence of total unrecoverable occlusions in the circuit and disconnections of the circuit, which can cause the controller to interpret that blood loss is occurring through the extracorporeal circuit to the external environment and stop the pump.

The controller may also compensate for variances in flow restrictions using control algorithms that apply two pressure targets: a withdrawal occlusion pressure target, and an infusion occlusion pressure target. By compensating for two control targets, the controller can monitor and discretely or simultaneously adjust for flow restrictions, e.g., partial occlusions, that occur in the withdrawal or infusion lines of the blood circuit. For example, if an occlusion occurs in the withdrawal vein, the pressure drop in the withdrawal line is sensed by the controller which in turn reduces the flow rate in accordance with an adjustable withdrawal pressure limit. The pump continues at a reduced speed, provided that the variable pressure vs. flow limit is satisfied and the boundary limits of the pressure vs. flow relationship are not exceeded. The controller may be required to stop the pump entirely, if the blood does not flow sufficiently (with acceptable pressure) at any pump speed. In such a condition, the controller will slow the pump to a stop as the withdrawal pressure target decreases. When the flow drops below a preprogrammed limit for a preprogrammed time, the pump will also be stopped by the flow controller and the user alarm will be activated.

In the event of a withdrawal pressure occlusion that terminates flow, the flow controller will temporarily reverse the flow of the pump in an attempt to remove the withdrawal occlusion. The occlusion algorithms are still active during this maneuver, and will also terminate flow if the occlusion cannot be removed. The volume displacement of the pump is limited to a specific number of revolutions to ensure that the pump does not infuse air into the patient.

With respect to the infusion pressure target, if a partial occlusion occurs in the infusion vein, the pressure controller detects a pressure rise in the return line and reduces the infusion rate. The controller will continue to reduce the pump speed and reduce the pressure in the infusion line. If the occlusion is total, the controller will quickly reduce the pump speed to a stop and avoid excessive pressure being applied to the infusion vein. The controller may also activate an alarm whenever the pump speed is stopped (or reduced to some lower speed level).

An application of the controller is in an extracorporeal blood system that includes a filter and blood pump in a blood circuit. This system extracts excess fluid from the blood of a fluid overloaded patient. The amount of excess fluid that is withdrawn from the blood is set by the operator at a clinically relevant rate to relieve the overloaded condition of the patient. The system accesses the peripheral veins of the patient, and avoids the need to access central venous blood. The filter system provides a simple method for controlling blood extraction from a peripheral vein. Thus, the blood filtering system could be used in a physician's clinic and outside of an ICU (intensive care unit of a hospital).

The blood filter system may provide an acceptable level of invasiveness, e.g., minimally invasive, for a fluid removal treatment in the desired environment and patient population via a peripheral vein preferably in an arm of a patient. Such access is commonly established by a nurse in order to draw blood or to infuse drugs. The filter system may withdraw up to 80% or intermittently up to 100% of the available blood fluid flow from the vein without causing the vein to collapse. Because of its reduced invasiveness, the filter system does not require an ICU or a special dialysis setting to be administered to a patient. If an apparatus for slow continuous ultrafiltration was available that would draw and re-infuse blood into the body using the access site similar to a common intravenous (IV) therapy, such a device would have a widespread clinical use.

The controller/filter system further provides a mechanism for maintaining patient safety while preventing false alarms when blood pressure measurements are made with or without the use of a blood pressure cuff.

SUMMARY OF THE DRAWINGS

A preferred embodiment and best mode of the invention is illustrated in the attached drawings that are described as follows.

DETAILED DESCRIPTION OF THE INVENTION

Figure 1:
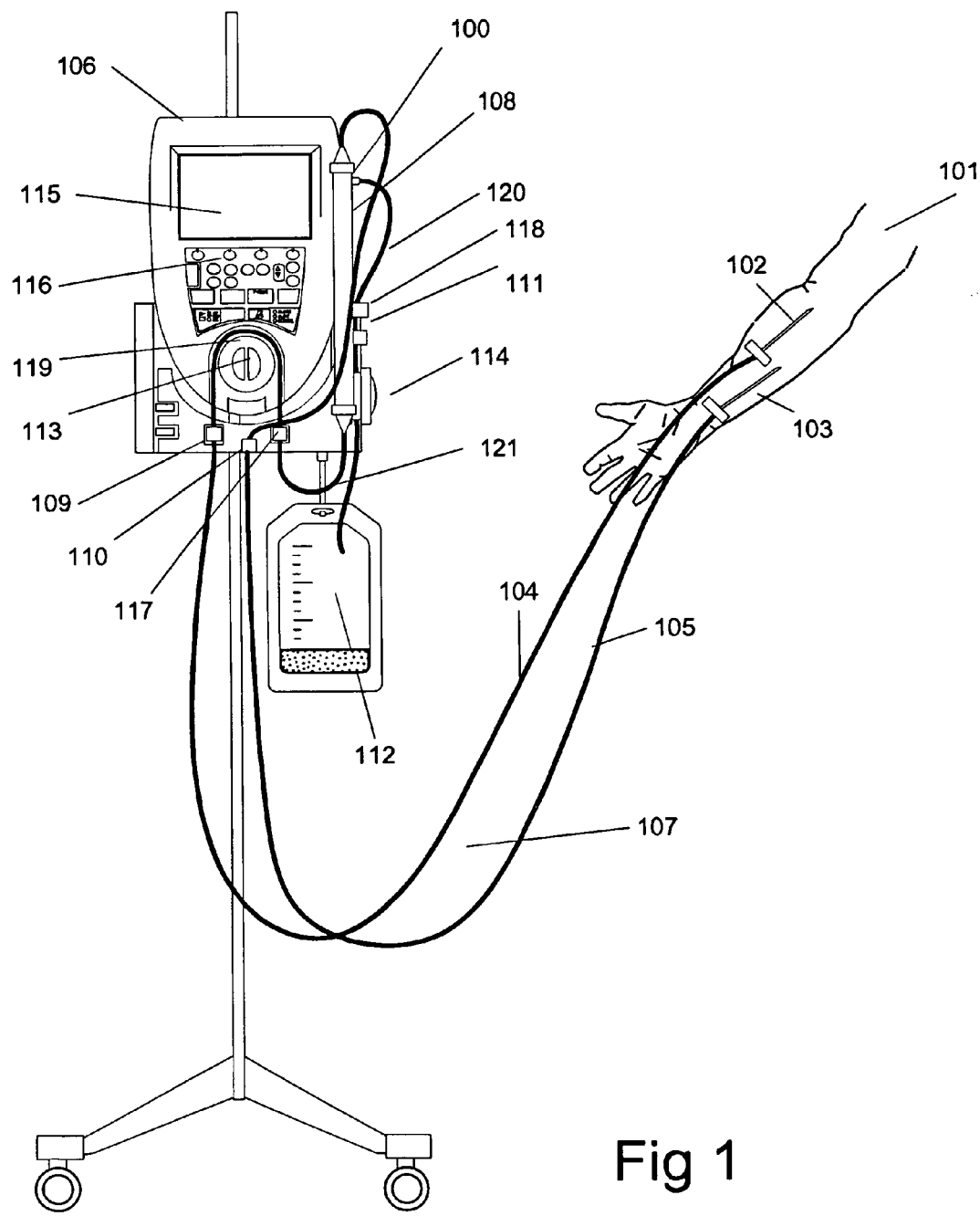
FIG. 1 illustrates the treatment of a patient with an ultrafiltration system using a controller in accordance with the present invention to monitor and control pressure and flow in an extracorporeal blood circuit.

A pump controller has been developed which may be incorporated in an extracorporeal blood circuit system. This system in an exemplary embodiment withdraws blood from a peripheral vein of a patient, processes the blood, e.g., passes the blood through a pump and filter, and returns the blood to the same or another peripheral vein. The pump controller monitors the blood pressure in the blood circuit and adjusts the speed of the pump (and hence the blood flow rate through the circuit) to comply with multiple limits on the pressure level and flow rates in the circuit. In addition, the controller promptly reacts to any changes in the pressure in the circuit.

The withdrawal and infusion of blood from a peripheral vein (or peripheral artery) in a mammalian patient (whether the patient is a human or other mammal) presents unique problems, which have been successfully addressed by the controller disclosed here. A peripheral vein in a human is a hollow tube, having approximately a 2 to 4 mm internal diameter. The wall of the vein is soft, flexible and not structurally self-supporting.

Blood pressure in the vein is required to keep the blood passage open and blood flowing through the vein. In a human vein, normal blood pressure in a vein is between 5 and 20 mmHg (millimeters of mercury). The blood flow through a peripheral vein generally ranges between 50 and 200 ml/min (milliliters per minute). Maintaining adequate pressure in a blood vessel from which blood is being withdrawn ensures that the vessel remains open to the flow of blood. The vein will collapse if the pressure drops excessively in a blood vessel, e.g., a vein. If the pressure in the vein becomes sub-atmospheric, the outside atmospheric pressure acting on the body will cause the vein to collapse.

An extracorporeal blood circuit draws blood from a peripheral vein (or artery) by applying a low pressure to a blood withdrawal tube attached to a catheter inserted into the vein. The pressure in the withdrawal tube is lower than the blood pressure in the vein. Due to this low pressure, some blood in the vein is drawn into the catheter and withdrawal tube. The lower pressure in the withdrawal tube and catheter is created by a pump in the blood circuit system that draws blood through the circuit and, in doing so, reduces the pressure in the withdrawal tube that is upstream of the pump. The reduced pressure in the withdrawal tube also reduces the pressure in the catheter and in the peripheral vein in which the catheter needle is inserted.

The reduced pressure in the vein near the catheter creates a potential risk of withdrawing blood from a peripheral vein too quickly and collapsing the vein. If the rate of blood flow into the withdrawal catheter is too great, the blood pressure in the vein will drop below that pressure required to keep the vein open and the vein will begin to collapse. As the vein collapses around the catheter, the blood flow into the catheter and the blood circuit is gradually reduced due to restrictions ("occlusions") in the collapsing vein. As the blood flow into the blood circuit decreases, the pressure in the withdrawal line drops further because the pump (if it remains at a constant speed) is still attempting to pull blood through the circuit at a constant rate. Thus, the pump can accelerate the collapse of the withdrawal vein by exacerbating the pressure drop in the vein, unless the speed of the pump is reduced before the vein fully collapses.

The novel pressure controller disclosed here prevents complete vein collapse by reducing the blood withdrawal flow rate in response to a pressure drop in a withdrawal tube. If the vein collapses nevertheless intermittently, the controller facilitates recovery and continues the blood withdrawal. A pressure sensor in the withdrawal tube monitors the blood pressure in real time. If and when a pressure drop is detected which exceeds the specified allowed limit in the withdrawal line, the controller (which receives and processes the pressure sensor signal) slows the blood pump to reduce the flow rate of blood being withdrawn from the peripheral vein. By slowing the withdrawal flow, the pressure in the withdrawal line and peripheral vein near the catheter may return to a higher level. This pressure increase will hopefully be sufficient to prevent vein collapse, before it actually occurs and allow for a continued withdrawal blood flow (albeit at a reduced withdrawal flow). However, if the pressure in the withdrawal line does not sufficiently elevate and the vein continues to fully collapse, the controller will detect the continued low pressure in the withdrawal line and continue to reduce the pump flow until the pump stops.

An embodiment of the present invention is a pump controller in an intravenous blood filtering system that withdraws blood from peripheral blood vessels. The controller includes a microprocessor and memory for storing data and software control algorithms. The microprocessor receives input signals from pressure sensors regarding the blood and ultrafiltrate pressures in the extracorporeal circuit, and from the pump regarding the pump speed. The microprocessor processes these input signals, applies the control algorithms and generates control signals that regulate the pump and hence the flow rate of blood and/or ultrafiltrate through the circuit.

The controller may regulate blood withdrawn from a peripheral vein to a flow rate in a normal range of 0 to 150 ml/min (milliliters per minute). An operator may select a maximum withdrawal flow rate within this normal pressure range at which the blood filtering system is to operate. The controller will maintain the flow rate at or near the desired flow rate, provided that there is compliance with a pressure vs. flow rate limit control algorithm. The controller maintains the withdrawal blood flow rate at the selected maximum flow rate, but automatically reduces the flow rate if the pressure in the system falls below a pressure limit for the actual flow rate. Thus, if there develops a partial flow restriction in the withdrawal vein or in the extracorporeal system, the controller will react by reducing the flow rate.

The controller optimizes blood flow at or below a preset maximum flow rate in accordance with one or more pressure vs. flow algorithms. These algorithms may be stored in memory of the controller which includes a processor, e.g., microprocessor; memory for data and program storage; input/output (I/O) devices for interacting with a human operator, for receiving feedback signals, e.g., pressure signals, from the blood circuit and possibly other systems, e.g., patient condition, and for issuing commands to control the pump speed; and data busses to allow the controller components to communicate with one another.

The control algorithms may include (without limitations): maximum flow settings for an individual patient treatment that is entered by the operator, a data listing of acceptable withdrawal/line pressures for each of a series of flow rates, and mathematical equations, e.g., linear, which correlates acceptable pressure to a flow rate. The algorithms may be determined for each particular make or model of an extraction and infusion extracorporeal blood system. In the present embodiment, the pressure vs. flow rate curves for occlusion and disconnect for the specified blood circuits are preprogrammed into the system.

Feedback signals are also used by the controller to confirm that the control algorithms are being satisfied. A real time pressure sensor signal from the withdrawal tube may be transmitted (via wire or wireless) to the controller. This pressure signal is applied by the controller as a feedback signal to compare the actual pressure with the pressure limits stored in memory of the controller for the current flow rate through the blood circuit. Based on this comparison, the controller sends control commands to adjust the speed of the pump motor, which controls the withdrawal and infusion pressures in the blood circuit. Using the pressure feedback signal, the controller ensures that the flow rate in the circuit complies with the variable pressure limits. Moreover, the pressure is monitored in real time every 10 ms so that the controller may continually determine whether the flow rate/pressure is acceptable. This is achieved by looking at the average flow rate over a consecutive one second period, and if the flow is less than a preset rate, the pump is stopped.

The exemplary apparatus described here is an ultrafiltration apparatus designed for the extraction of plasma water from human blood. To extract plasma water (ultrafiltrate), the apparatus includes a filter. The filter has a membrane that is permeable to water and small molecules, and impermeable to blood cells, proteins and other large solutes particles. FIG. 1 illustrates the treatment of a fluid overloaded patient with an ultrafiltration apparatus 100. The patient 101, such as a human or other mammal, may be treated while in bed or sitting in a chair and may be conscious or asleep. The apparatus may be attached to the patient in a doctor's office, an outpatient clinic, and may even be suitable for use at home (provided that adequate supervision of a doctor or other medically trained person is present). The patient need not be confined to an intensive care unit (ICU), does not require surgery to be attached to the ultrafiltration apparatus, and does not need specialized care or the continual presence of medical attendants.

To initiate ultrafiltration treatment, two standard 18 G (gage) catheter needles, a withdrawal needle 102 and a infusion (return) needle 103, are introduced into suitable peripheral veins (on the same or different arms) for the withdrawal and return of the blood. This procedure of inserting needles is similar to that used for inserting catheter needles to withdraw blood or for intravenous (IV) therapy. The needles are attached to withdrawal tubing 104 and return tubing 105, respectively. The tubing may be secured to skin with adhesive tape.

The ultrafiltration apparatus includes a blood pump console 106 and a blood circuit 107. The console includes two rotating roller pumps that move blood and ultrafiltrate fluids through the circuit, and the circuit is mounted on the console. The blood circuit includes a continuous blood passage between the withdrawal catheter 102 and the return catheter 103. The blood circuit includes a blood filter 108; pressure sensors 109 (in withdrawal tube), 110 (in return tube) and 111 (in filtrate output tube); an ultrafiltrate collection bag 112 and tubing lines to connect these components and form a continuous blood passage from the withdrawal to the infusion catheters an ultrafiltrate passage from the filter to the ultrafiltrate bag. The blood passage through the circuit is preferably continuous, smooth and free of stagnate blood pools and air/blood interfaces. These passages with continuous airless blood flow reduce the damping of pressure signals by the system and allows for a higher frequency response pressure controller, which allows the pressure controller to adjust the pump velocity more quickly to changes in pressure, thereby maintaining accurate pressure control without causing oscillation. The components of the circuit may be selected to provide smooth and continuous blood passages, such as a long, slender cylindrical filter chamber, and pressure sensors having cylindrical flow passage with electronic sensors embedded in a wall of the passage. The circuit may come in a sterile package and is intended that each circuit be used for a single treatment. A more detailed description of an exemplary blood circuit is included in commonly owned and co-pending U.S. Pat. No. 6,887,214 (U.S. patent application Ser. No. 09/660,195, filed Sep. 12, 2000), which is incorporated by reference.

The circuit mounts on the blood and ultrafiltrate pumps 113 (for blood passage) and 114 (for filtrate output of filter). The circuit can be mounted, primed and prepared for operation within minutes by one operator. The operator of the blood ultrafiltration apparatus 100, e.g., a nurse or medical technician, sets the maximum rate at which fluid is to be removed from the blood of the patient. These settings are entered into the blood pump console 106 using the user interface, which may include a display 115 and control panel 116 with control keys for entering maximum flow rate and other controller settings. Information to assist the user in priming, setup and operation is displayed on the LCD (liquid crystal display) 115.

The ultrafiltrate is withdrawn by the ultrafiltrate pump 114 into a graduated collection bag 112. When the bag is full, ultrafiltration stops until the bag is emptied. The controller may determine when the bag is filled by determining the amount of filtrate entering the bag based on the volume displacement of the ultrafiltrate pump in the filtrate line and filtrate pump speed, or by receiving a signal indicative of the weight of the collection bag. As the blood is pumped through the circuit, an air detector 117 monitors for the presence of air in the blood circuit. A blood leak detector 118 in the ultrafiltrate output monitors for the presence of a ruptured filter. Signals from the air detector and/or blood leak detector may be transmitted to the controller, which in turn issues an alarm if a blood leak or air is detected in the ultrafiltrate or blood tubing passages of the extracorporeal circuit.

Figure 2:
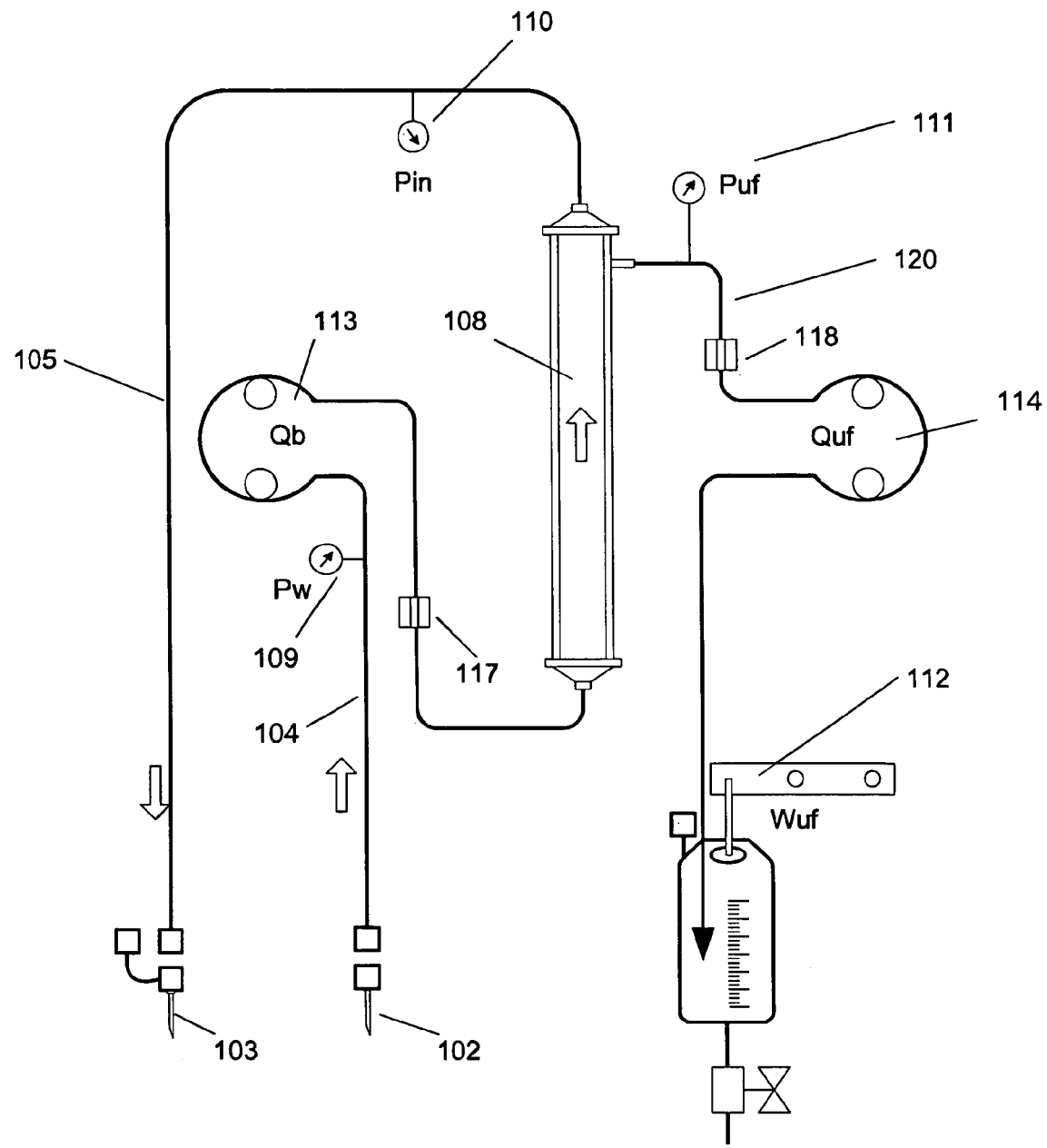
FIG. 2 illustrates the operation and fluid path of the blood circuit shown in FIG. 1.

FIG. 2 illustrates the operation and fluid paths of blood and ultrafiltrate through the blood circuit 107. Blood is withdrawn from the patient through an 18 Gage or similar withdrawal needle 102. The withdrawal needle 102 is inserted into a suitable peripheral vein in the patient's arm. The blood flow from the peripheral vein into the withdrawal tubing 104 is dependent on the fluid pressure in that tubing which is controlled by a roller pump 113 on the console 106.

The length of withdrawal tubing between the withdrawal catheter and pump 113 may be approximately two meters. The withdrawal tubing and the other tubing in the blood circuit may be formed of medical PVC (polyvinyl chloride) of the kind typically used for IV (intravenous) lines which generally has an internal diameter (ID) of 3.2 mm. IV line tubing may form most of the blood passage through the blood circuit and have a generally constant ID throughout the passage.

The pressure sensors may also have a blood passage that is contiguous with the passages through the tubing and the ID of the passage in the sensors may be similar to the ID in the tubing. It is preferable that the entire blood passage through the blood circuit (from the withdrawal catheter to the return catheter) have substantially the same diameter (with the possible exception of the filter) so that the blood flow velocity is substantially uniform and constant through the circuit. A benefit of a blood circuit having a uniform ID and substantially continuous flow passages is that the blood tends to flow uniformly through the circuit, and does not form stagnant pools within the circuit where clotting may occur.

The roller blood pump 113 is rotated by a brushless DC motor housed within the console 106. The pump includes a rotating mechanism with orbiting rollers that are applied to a half-loop 119 in the blood passage tubing of the blood circuit. The orbital movement of the rollers applied to tubing forces blood to move through the circuit. This half-loop segment may have the same ID as does the other blood tubing portions of the blood circuit. The pump may displace approximately 1 ml (milliliter) of blood through the circuit for each full orbit of the rollers. If the orbital speed of the pump is 60 RPM (revolutions per minute), then the blood circuit may withdraw 60 ml/min of blood, filter the blood and return it to the patient. The speed of the blood pump 113 may be adjusted by the controller to be fully occlusive until a pressure limit of 15 psig (pounds per square inch above gravity) is reached. At pressures greater than 15 psig, the pump rollers relieve because the spring force occluding the tube will be exceeded and the pump flow rate will no longer be directly proportional to the motor velocity because the rollers will not be fully occlusive and will be relieving fluid. This safety feature ensures the pump is incapable of producing pressure that could rupture the filter.

The withdrawal pressure sensor 109 is a flow-through type sensor suitable for blood pressure measurements. It is preferable that the sensor have no bubble traps, separation diaphragms or other features included in the sensor that might cause stagnant blood flow and lead to inaccuracies in the pressure measurement. The withdrawal pressure sensor is designed to measure negative (suction) pressure down to −400 mm Hg.

All pressure measurements in the fluid extraction system are referenced to both atmospheric and the static head pressure offsets. The static head pressure offsets arise because of the tubing placement and the pressure sensor height with respect to the patient connection. The withdrawal pressure signal is used by the microprocessor control system to maintain the blood flow from the vein and limit the pressure. Typically, a peripheral vein can continuously supply between 60-200 ml/min of blood. This assumption is supported by the clinical experience with plasma apheresis machines.

A pressure sensor 121 may be included in the circuit downstream of the pumps and upstream of the filter. Blood pressure in the post pump, pre-filter segment of the circuit is determined by the patient's venous pressure, the resistance to flow generated by the infusion catheter 103, resistance of hollow fibers in the filter assembly 108, and the flow resistance of the tubing in the circuit downstream of the blood pump 113. At blood flows of 40 to 60 ml/min, in this embodiment, the pump pressure may be generally in a range of 300 to 500 mm Hg depending on the blood flow, condition of the filter, blood viscosity and the conditions in the patient's vein.

The filter 108 is used to ultrafiltrate the blood and remove excess fluid from the blood. Whole blood enters the filter and passes through a bundle of hollow filter fibers in a filter canister. There may be approximately 700 to 900 hollow fibers in the bundle, and each fiber is a filter. In the filter canister, blood flows through an entrance channel to the bundle of fibers and enters the hollow passage of each fiber. Each individual fiber has approximately 0.2 mm internal diameter. The walls of the fibers are made of a porous material. The pores are permeable to water and small solutes, but are impermeable to red blood cells, proteins and other blood components that are larger than 50,000-60,000 Daltons. Blood flows through the fibers tangential to the surface of the fiber filter membrane. The shear rate resulting from the blood velocity is high enough such that the pores in the membrane are protected from fouling by particles, allowing the filtrate to permeate the fiber wall. Filtrate (ultrafiltrate) passes through the pores in the fiber membrane (when the ultrafiltrate pump is rotating), leaves the fiber bundle, and is collected in a filtrate space between the inner wall of the canister and outer walls of the fibers.

The membrane of the filter acts as a restrictor to ultrafiltrate flow. An ultrafiltrate pressure transducer (Puf) 111 is placed in the ultrafiltrate line upstream of the ultrafiltrate roller pump 114. The ultrafiltrate pump 114 is rotated at the prescribed fluid extraction rate which controls the ultrafiltrate flow from the filter. Before entering the ultrafiltrate pump, the ultrafiltrate passes through approximately 20 cm of plastic tubing 120, the ultrafiltrate pressure transducer (Puf) and the blood leak detector 118. The tubing is made from medical PVC of the kind used for IV lines and has internal diameter (ID) of 3.2 mm. The ultrafiltrate pump 114 is rotated by a brushless DC motor under microprocessor control. The pump tubing segment (compressed by the rollers) has the same ID as the rest of the ultrafiltrate circuit.

The system may move through the filtrate line approximately 1 ml of filtrate for each full rotation of the pump. A pump speed of 1.66 RPM corresponds to a filtrate flow of 1.66 ml/min, which corresponds to 100 ml/hr of fluid extraction. The ultrafiltrate pump 114 is adjusted at the factory to be fully occlusive until a pressure limit of 15 psig is reached. The rollers are mounted on compression springs and relieved when the force exerted by the fluid in the circuit exceeds the occlusive pressure of the pump rollers. The circuit may extract 100 to 500 ml/hr of ultrafiltrate for the clinical indication of fluid removal to relieve fluid overload.

After the blood passes through the ultrafiltrate filter 108, it is pumped through a two meter infusion return tube 105 to the infusion needle 103 where it is returned to the patient. The properties of the filter 108 and the infusion needle 103 are selected to assure the desired TMP (Trans Membrane Pressure) of 150 to 250 mm Hg at blood flows of 40-60 ml/min where blood has hematocrit of 35 to 45% and a temperature of 34° C. to 37° C. The TMP is the pressure drop across the membrane surface and may be calculated from the pressure difference between the average filter pressure on the blood side and the ultrafiltration pressure on the ultrafiltrate side of the membrane. Thus, TMP=((Inlet Filter Pressure+Outlet Filter Pressure)/2)−Ultrafiltrate Pressure.

The blood leak detector 118 detects the presence of a ruptured/leaking filter, or separation between the blood circuit and the ultrafiltrate circuit. In the presence of a leak, the ultrafiltrate fluid will no longer be clear and transparent because the blood cells normally rejected by the membrane will be allowed to pass. The blood leak detector detects a drop in the transmissibility of the ultrafiltrate line to infrared light and declares the presence of a blood leak.

The pressure transducers Pw (withdrawal pressure sensor 109), Pin (infusion pressure sensor 110) and Puf (filtrate pressure sensor 111) produce pressure signals that indicate a relative pressure at each sensor location. Prior to filtration treatment, the sensors are set up by determining appropriate pressure offsets. These offsets are used to determine the static pressure in the blood circuit and ultrafiltrate circuit due to gravity. The offsets are determined with respect to atmospheric pressure when the blood circuit is filled with saline or blood, and the pumps are stopped. The offsets are measures of the static pressure generated by the fluid column in each section, e.g., withdrawal, return line and filtrate tube, of the circuit. During operation of the system, the offsets are subtracted from the raw pressure signals generated by the sensors as blood flows through the circuit. Subtracting the offsets from the raw pressure signals reduces the sensitivity of the system to gravity and facilitates the accurate measurement of the pressure drops in the circuit due to circuit resistance in the presence of blood and ultrafiltrate flow. Absent these offsets, a false disconnect or occlusion alarm could be issued by the monitor CPU (714 in FIG. 7) because, for example, a static 30 cm column of saline/blood will produce a 22 mm Hg pressure offset.

The pressure offset for a particular sensor is a function of the fluid density "$\rho$", the height of the tube "h" and the earth's gravitational constant "g":

$$P\text{offset} = \rho * g * h$$

where "$\rho$" and "g" are constants and, thus, pressure offsets are a function of the sensor position. The pressure offsets are not experienced by the patient. Proof of this is when a 3.2 mm ID tube filled with water with its top end occluded (pipette) does not allow the water to flow out. This means that the pressure at the bottom of the tube is at 0 mm Hg gage. In order to normalize the offset pressures, the offsets are measured at the start of operation when the circuit is fully primed and before the blood pump or ultrafiltrate pump are actuated. The measured offsets are subtracted from all subsequent pressure measurements. Therefore, the withdrawal pressure Pw, the infusion pressure Pin and the ultrafiltrate pressure Puf are calculated as follows:

$$Pw = Pw\text{Gage} - Pw\text{Offset}$$

$$Pin = Pin\text{Gage} - Pin\text{Offset}$$

$$Puf = Puf\text{Gage} - Puf\text{Offset}$$

PwOffset, PinOffset and PufOffset are measured when the circuit is primed with fluid, and the blood and ultrafiltrate pumps are stopped. PwGage, PinGage and PufGage are measured in real time and are the raw, unadjusted gage pressure readings from the pressure transducers. To increase accuracy and to minimize errors due to noise, the offsets are checked for stability and have to be stable within 2 mm Hg for 1 second before an offset reading is accepted. The offset is averaged over 1 second to further reduce sensitivity to noise.

Figure 3:
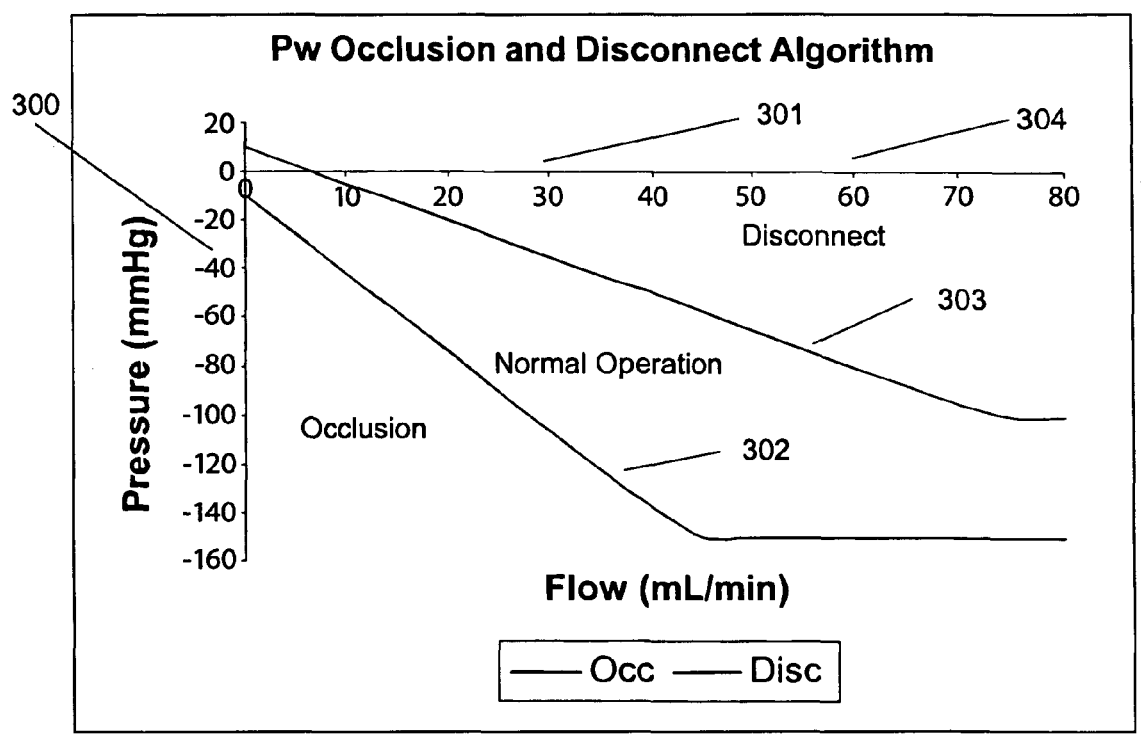
FIG. 3 is a chart of the withdrawal occlusion and disconnect limits applied by the controller.

FIG. 3 is a chart of pressure limits 300 in the blood circuit versus the blood flow rate 301 in the circuit. The chart shows graphically exemplary control algorithms for controlling pressure in the withdrawal line as a function of the actual blood flow. The blood flow rate is known, and calculated from the known pump speed. An occlusion control function 302 (PwOcc—Occlusion) provides a variable pressure limit vs. flow rate (sloped portion of PwOcc—Occlusion) for controlling the minimum pressure limit in the withdrawal line as a function of flow rate.

The maximum negative pressure (i.e., lowest suction level) in the withdrawal line is limited by an algorithm 303 (disconnect—PwDisc) which is used to sense when a disconnect occurs in the withdrawal line. The withdrawal line has a suction pressure (sub-atmospheric) pressure to draw blood from the peripheral artery. This suction pressure is shown as a negative pressure in mmHg in FIG. 3. If the actual suction pressure rises above a limit (PwDisc), then the controller may signal that a disconnect has occurred, especially if air is also detected in the blood circuit. The suction pressure in the withdrawal line is controlled to be between the occlusion and disconnect pressure limits 302, 303.

The maximum withdrawal resistance (PwOcc,—see the slope of line 302) for a given flow rate is described by the occlusion algorithm curve 302. This allowable occlusion pressure, PwOcc (401 in FIG. 4), increases as blood flow increases. This increase may be represented by a linear slope of flow rate vs. pressure, that continues, until a maximum flow rate 304 is reached. The occlusion algorithm curve is based on theoretical and empirical data with a blood Hct of 35% (maximum Hct expected in clinical operation), and the maximum expected resistance of the withdrawal needle and withdrawal blood circuit tube expected during normal operation when measured at Pw.

The withdrawal pressure sensor signal (Pw) is also applied to determine whether a disconnection has occurred in the withdrawal blood circuit between the withdrawal tubing 104 from the needle 102 or between the needle and the patient's arm, or a rupture in the withdrawal tubing. The control algorithm for detecting a disconnection is represented by PwDisc curve 303. This curve 303 represents the minimum resistance of the 18 Gage needle and withdrawal tubing, with a blood Hct of 25% (minimum Hct expected in clinical operation), at a temperature of 37° C. The data to generate this curve 303 may be obtained in vitro and later incorporated in the controller software.

During the device operation the measured withdrawal pressure (Pw) is evaluated in real time, for example, every 10 milliseconds, by the controller. Measured Pw is compared to the point on the curve 303 that corresponds to the current blood flow rate. A disconnection is detected when the pressure Pw at a given blood flow is greater than the pressure described by curve 303, and if air is detected in the blood circuit. If the withdrawal line becomes disconnected, the blood pump 113 will entrain air into the tubing due to the suction caused by the withdrawal pressure (Pw) when the blood pump is withdrawing blood. The pressure measured by the withdrawal pressure transducer Pw will increase (become less negative) in the presence of a disconnection because the resistance of the withdrawal line will decrease.

Figure 4:
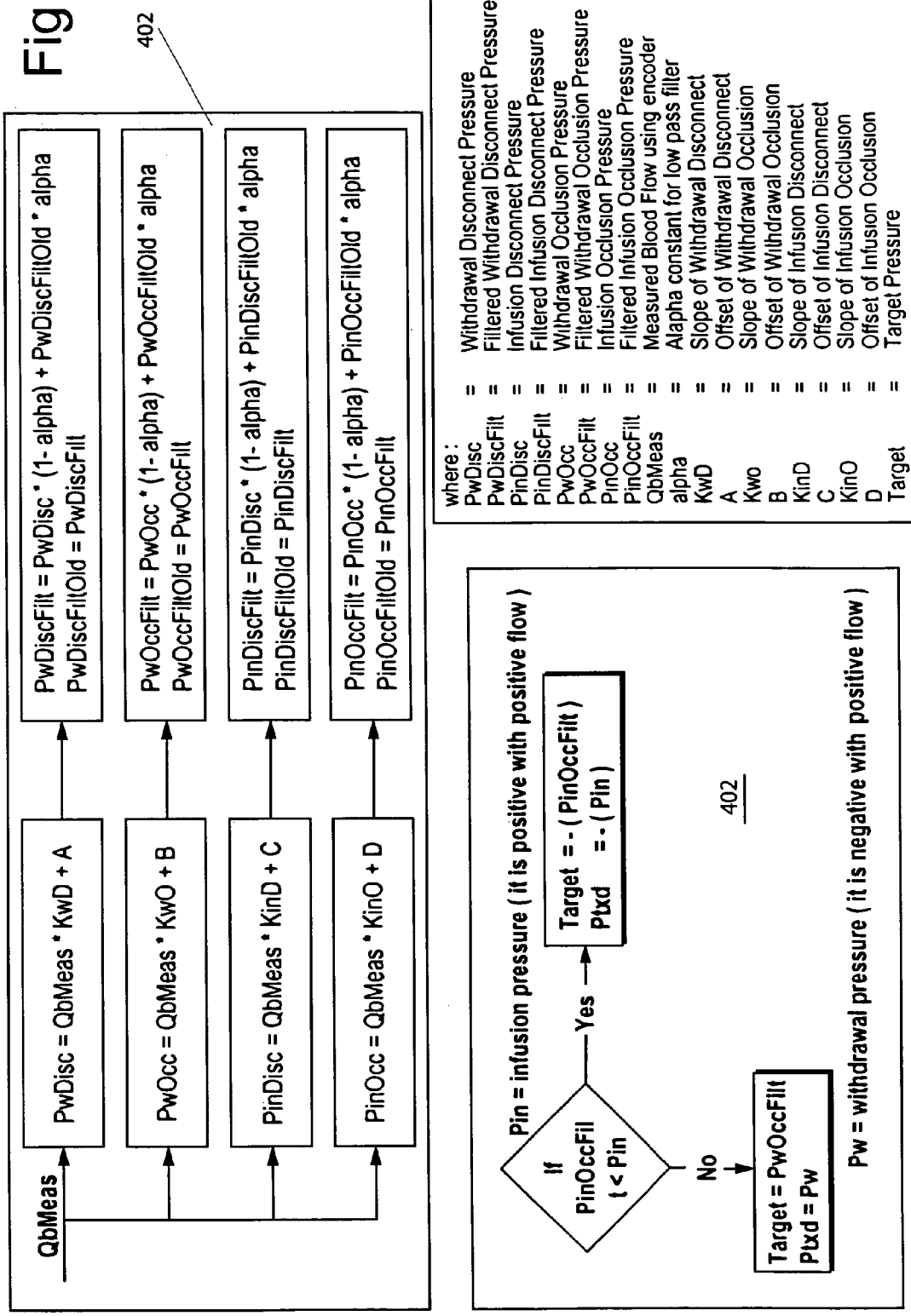
FIG. 4 is a flow chart of an algorithm to implement the occlusion and disconnect limits shown in FIGS. 3 and 6, and showing how the blood withdrawal and infusion occlusion and disconnect pressures are calculated as a function of measured blood flow.

FIG. 4 is a flow chart showing in mathematical terms the control algorithms shown in FIG. 3. The allowable occlusion pressure (PwOcc) 401 is determined as a function of blood flow (QbMeas). The blood flow (QbMeas) may be determined by the controller, e.g., controller CPU, based on the rotational speed of the blood pump and the known volume of blood that is pumped with each rotation of that pump, as is shown in the equation below:

$$PwOcc = Qb\text{Meas} * KwO + B$$

Where QbMeas is the measured blood flow, KwO is the withdrawal occlusion control algorithm 302, e.g., a linear slope of flow vs. pressure, and B is a pressure offset applied to the withdrawal occlusion, which offset is described below.

The expression for PwOcc is a linear equation to describe. PwOcc may also be implemented as a look up table where a known QbMeas is entered to obtain a value for PwOcc. In addition, the expression for PwOcc may be a second order polynomial in the presence of turbulent flow. The expression for PwOcc to be chosen in a particular implementation will be based upon the characteristics of the tube and the presence of laminar or turbulent flow.

The PwOcc signal may be filtered with a 0.2 Hz low pass filter to avoid false occlusion alarms, as indicated in the following sequential pair of equations.

$$PwOcc\text{Filt} = PwOcc * (1 - \text{alpha}) + PwOcc\text{FiltOld} * \text{alpha}$$

Where alpha=exp(−t/Tau)

Where t=discrete real time sample interval in seconds and The time constant Tau=1/(2*PI*Fc)

Where PI=3.1416 and Fc is equal to the cutoff frequency of the first order low pass filter in Hz.

Thus, for a 0.2 Hx filter, Tau=0.7957 therefore alpha=0.9875

Where PwOccFilt is the current calculated occlusion pressure limit for the actual flow rate, after being filtered. PwOccFiltOld is the previous calculated occlusion pressure, and "alpha" is a constant of the low pass filter. Thus, PwOccFiltOld=PwOccFilt, for each successive determination of PwOccfilt.

Similar determinations are made for the calculated pressure limits for the filtered withdrawal disconnect limit (PwDiscFilt), filtered infusion disconnect limit (PinDiscFilt) and filtered infusion occlusion limit (PinOccFilt).

The PwDisc curve 303, shown in FIG. 3 is described in equation form below and shown in 401 of FIG. 4. The withdrawal disconnection pressure, PwDisc is calculated as a function (KwD) of blood flow, QbMeas which is measured blood flow calculated from the encoder pump speed signal.

$$PwDisc=QbMeas*KwD+A$$

Where A is a pressure constant offset, and KwD represents the slope of the PwDisc curve 303. In addition, the PwDisc (withdrawal pressure limit for disconnect) is filtered with a 0.2 Hz low pass filter to avoid false disconnect alarms, reference 401 in FIG. 4.

PwDisc is a linear equation to describe. PwDisc may also be implemented as a look up table where a known QbMeas is entered to obtain a value for QbMeas. In addition, the expression for PwDisc may be a second order polynomial in the presence of turbulent flow. The expression for PwDisc to be chosen in a particular implementation will be based upon the characteristics of the tube and the presence of laminar or turbulent flow.

$$PwDiscFilt=PwDisc*(1-alpha)+PwDiscFiltOld*alpha$$

$$PwDiscFiltOld=PwDiscFilt$$

Where alpha is a function of the filter.

The air detector 117 detects the presence of air when entrained. If the withdrawal pressure (Pw) exceeds (is less negative than) the disconnect pressure (PwDisc) 303 and air is detected in the blood circuit by the air detector, then the controller declares a withdrawal disconnection, and the blood pump and the ultrafiltrate pump are immediately stopped. This logic function is expressed as:

If (*Pw*>*Pw*DiscFilt AND AirDetected=TRUE)

{then Declare a withdrawal disconnect}

The above logic function is a reliable detection of a withdrawal line disconnection, while avoiding false alarms due to blood pressure measurements with blood pressure cuffs. For example, a false alarm could be generated when blood pressure cuffs are pressurized which causes an increased venous pressure and in turn lower withdrawal pressure. The lower withdrawal pressure caused by a blood pressure cuff might be interpreted by the controller as a disconnection resulting in false alarms, except for the logic requirement of air being detected.

Figure 6:
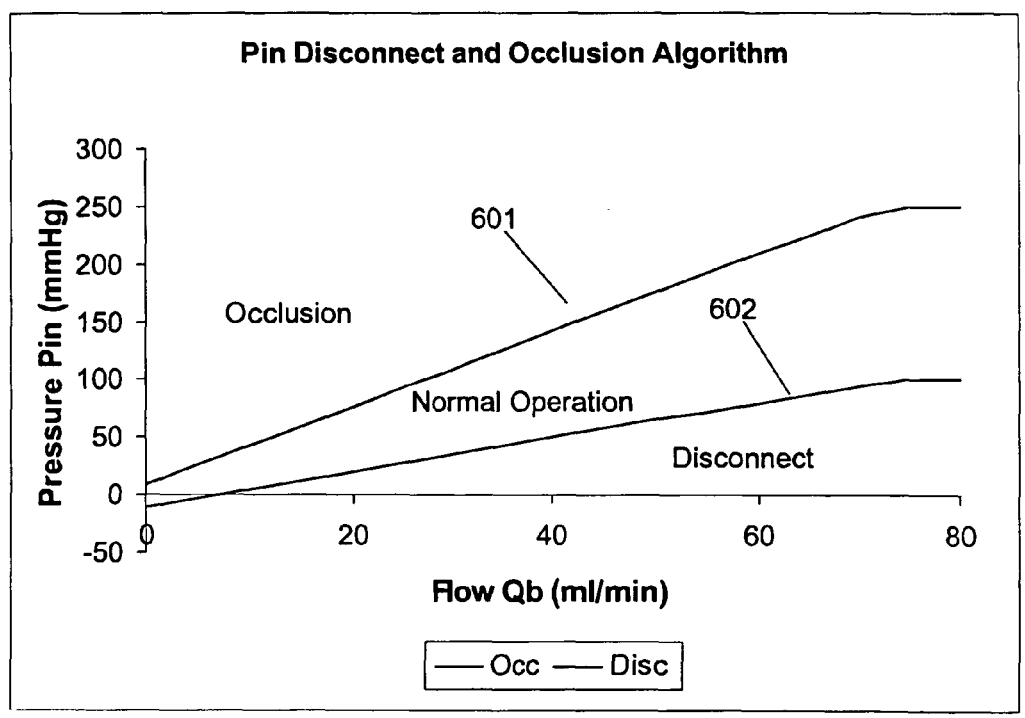
FIG. 6 is a chart of infusion occlusion and disconnect limits for the ultrafiltration system.

The occlusion and disconnect pressure limits for the return (infusion) line are graphically shown in FIG. 6. These calculations are made in a similar manner as described above for determining PwOccFilt. The infusion-occlusion pressure limit (PinOcc) 401 is calculated as a function of blood flow (QbMeas) where QbMeas is actual blood flow calculated from the pump speed feedback signal.

PinOcc=QbMeas*KwO+B, where KwO is the factor for converting (see FIG. 6, Occlusion line 601) the actual blood flow rate to a pressure limit. The expression for PinOcc is a linear equation to describe. PinOcc may also be implemented as a look up table where a known QbMeas is entered to obtain a value for PinOcc. In addition, the expression for PinOcc may be a second order polynomial in the presence of turbulent flow. The expression for PinOcc to be chosen in a particular implementation will be based upon the characteristics of the tube and the presence of laminar or turbulent flow.

PinOcc is filtered with a 0.2 Hz low pass filter to avoid false disconnect alarms.

$$PinOccFilt=PinOcc*(1-alpha)+PinOccFiltOld*alpha$$

$$PinOccFiltOld=PinOccFilt$$

FIG. 4 also shows the interaction of the control algorithms for withdrawal occlusion (PwOccFilt) and the infusion occlusion (PinOccFilt). The control theory for having two control algorithms applicable to determining the proper flow rate is that only one of the control algorithms will be applied to determine a target flow rate at any one time. To select which algorithm to use, the controller performs a logical "If-Then operation" 402 that determines whether the target is to be the withdrawal occlusion or infusion occlusion algorithms. The criteria for the If-Then operation is whether the infusion line is occluded or not. If the infusion line is occluded, Pin is greater than PinOccFilt; therefore, the Target is set to PinOccFilt.

In particular, the infusion occlusion algorithm (PinOccFilt) is the target (Target) and infusion pressure (Pin) is applied as a feedback signal (Ptxd), only when the infusion pressure (Pin) exceeds the occlusion limit for infusion pressure (PinOccFilt). Otherwise, the Target is the occlusion withdrawal pressure limit (PwOccFilt) and the feedback signal is the withdrawal pressure (Pw).

The If-Then (402) algorithm is set forth below in a logic statement (see also the flow chart 402):

If (PinOccFilt<Pin)

{Then Target=−(PinOccFilt), and Ptxd=−(Pin)}

{Else Target=PwOccFilt and Ptxd=Pw}

A pressure controller (see FIG. 5 description) may be used to control the Ptxd measurement to the Target pressure. The Target pressure will be either the PinOccFilt or PwOccFilt limit based upon the IF statement described above.

Figure 5:
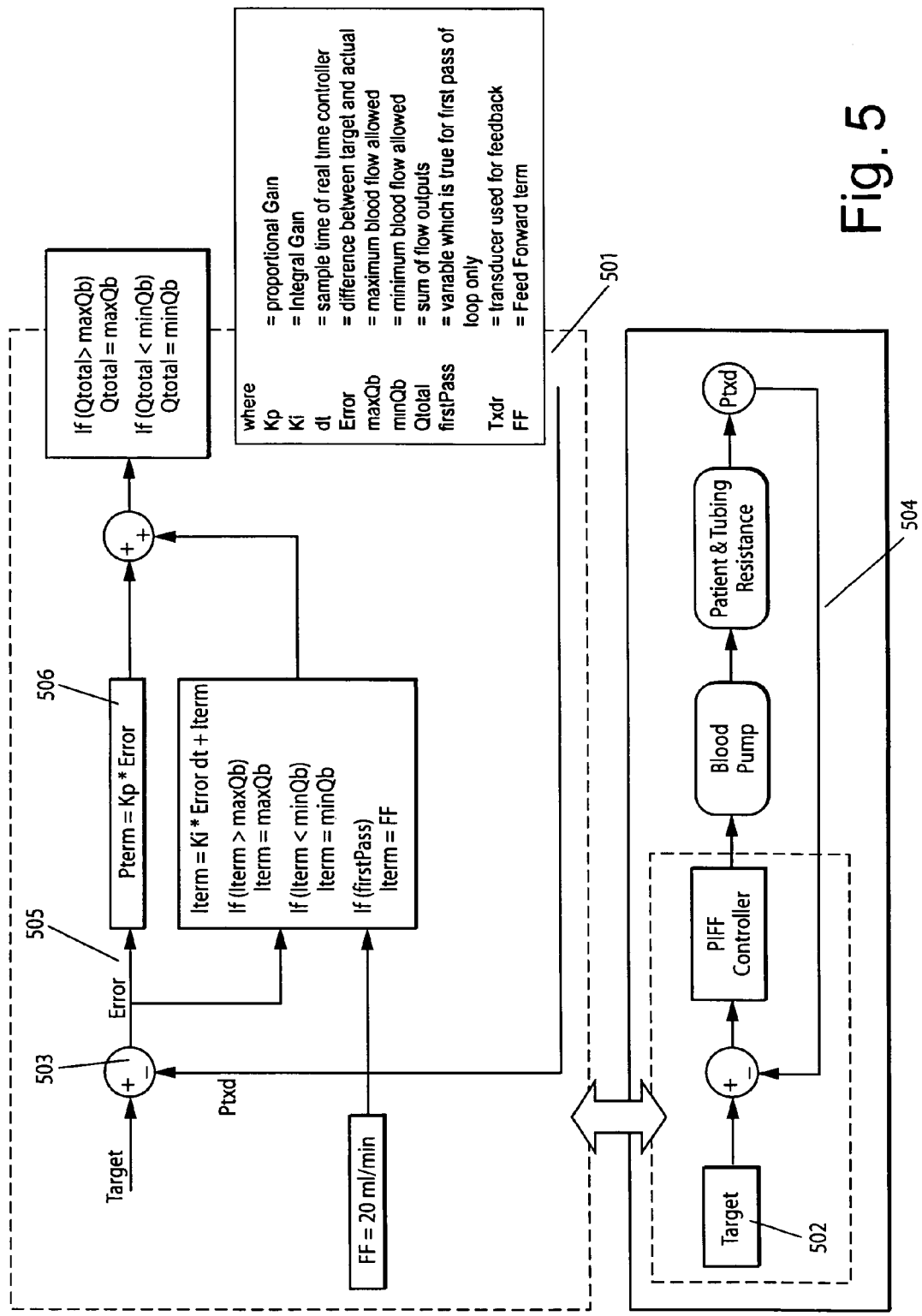
FIG. 5 is a flow chart of an algorithm showing a blood withdrawal and infusion PIFF pressure control algorithm to be implemented by the controller.

FIG. 5 includes a functional diagram of a PIFF (Proportional Integral Feed Forward) pressure controller 501 for the ultrafiltration apparatus 100, and shows how the PIFF operates to control pressure and flow of blood through the circuit. Controllers of the PIFF type are well known in the field of "controls engineering". The PIFF pressure controller 501 controls the withdrawal pressure to the prescribed target pressure 502, which is the filtered withdrawal occlusion pressure limit (PwOccFilt), by adjusting the blood pump flow rate. The PIFF may alternatively use as a target the limit for infusion pressure (PinOccFilt). The target pressure 502 limit is compared 503 to a corresponding actual pressure 504, which is withdrawal pressure (Pw) if the target is PwOccFilt and is infusion pressure (Pin) if the target is PinOccFilt. The actual pressure is applied as a feedback signal (Ptxd) in the PIFF. The logical compare operation 503 generates a difference signal (Error) 505 that is processed by the PIFF.

The PIFF determines the appropriate total flow rate (Qtotal) based on the difference signal 505, the current flow rate, the current rate of increase or decrease of the flow rate, and the flow rate limit. The PIFF evaluates the difference between the target pressure limit and actual pressure (feedback) with a proportional gain (Kp), an integral gain (Ki) and a feed forward term (FF). The proportional gain (Kp) represents the gain applied to current value of the error signal 505 to generate a proportional term (Pterm) 506, which is one component of the sum of the current desired flow (Qtotal). The integral gain (Ki) is the other component of Qtotal, and is a gain applied to the rate at which the error signal varies with time (error dt). The product of the integral gain and the error dt (Iterm) is summed with the previous value of Iterm to generate a current item value. The current Iterm value and Pterm value are summed, checked to ensure that the sum is within flow limits, and applied as the current desired total flow rate (Qtotal). This desired flow rate (Qtotal) is then applied to control the blood pump speed, and, in turn, the actual flow rate through the blood circuit.

The gain of the PIFF pressure controller Kp and Ki have been chosen to ensure stability when controlling with both withdrawal and infusion pressures. The same PIFF controller is used for limiting withdrawal and infusion pressures. None of the controller terms are reset when the targets and feedback transducers are switched. This ensures that there are no discontinuities in blood flow and that transitions between control inputs are smooth and free from oscillation. Thus, when the PIFF pressure controller switches from controlling on withdrawal pressure top infusion pressure the blood pump does not stop, it continues at a velocity dictated by the pressure control algorithm.

The proportional and integral gains (Kp and Ki) of the pressure controller are selected to ensure stability. Kp and Ki were chosen to ensure that pressure overshoots are less than 30 mmHg, and that the pressure waveform when viewed on a data acquisition system was smooth and free of noise. In general Kp may be increased until the noise level on the signal being controlled exceeds the desired level. Kp is then reduced by 30%. Ki is chosen to ensure the steady state error is eliminated and that overshoot is minimized. Both the integral term and the total flow output of the PIFF controller are limited to a maximum of 60 ml/min, in this embodiment.

In addition, in this embodiment the flow limits for the integral term and total flow output may be increased linearly starting at a maximum rate of 20 ml/min (FF). When the PIFF controller is initially started, the integral term (Iterm) is set equal to the feed forward term (FF), which may be 20 ml/min. Thus, 40 seconds are required to increase the flow limit from an initial setting (20 ml/min) to the maximum value of 60 ml/min. This 40 second flow increase period should be sufficient to allow the withdrawal vein to respond to increases in withdrawal flow rate. Limiting the rate of increase of the blood flow is needed because veins are reservoirs of blood and act as hydraulic capacitors. If a flow rate is increased too quickly, then a false high flow of blood can occur for short periods of time because flow may be supplied by the elastance of the vein (that determines compliance), and may not be true sustainable continuous flow much like an electrical capacitor will supply short surges in current.

This PIFF pressure controller controls pressure in real time, and will immediately reduce the pressure target if a reduction in flow occurs due to an occlusion. The target pressure is reduced in order to comply with the occlusion pressure limit, such as is shown in FIG. 3. Reducing the pressure target in the presence of an occlusion will lead to a further reduction in flow, which will result in a further reduction in the target pressure. This process limits the magnitude and duration of negative pressure excursions on the withdrawal side, and, therefore, exposure of the patient's vein to trauma. It also gives the withdrawal (or infusion) vein time to recover, and the patient's vein time to reestablish flow without declaring an occlusion.

When a withdrawal vein collapses, the blood pump will be stopped by the PIFF controller because the vein will have infinite resistance resulting in zero blood flow no matter to what pressure Pw is controlled. When the blood pump stops, the blood flow is reversed and blood is pumped into the withdrawal vein in an attempt to open that vein. When the blood pump is reversed, the withdrawal and infusion disconnect and occlusion algorithms are still active protecting the patient from exposure to high pressures and disconnects. When the blood pump flow is reversed the occlusion limits and disconnect limits are inverted by multiplying by negative 1. This allows the pump to reverse while still being controlled by maximum pressure limits.

If (Blood Pump is reversing)

{PwDiscFilt and PinDiscFilt and PwOccFilt and PwOccFilt are inverted}

Two (2) ml of blood may be infused into the withdrawal line and into the withdrawal peripheral vein by reversing the blood pump at 20 ml/min to ensure that the vein is not collapsed. The blood pump is stopped for 2 seconds and withdrawal is reinitiated. The controller issues an alarm to request that the operator check vein access after three automatic attempts of reversing blood flow into the withdrawal line. The blood circuit has a total volume of approximately 60 ml. The blood pump is limited to reversing a total volume of five ml thereby minimizing the possibility of infusing the patient with air.

The PIFF applies a maximum withdrawal flow rate (maxQb) and a minimum withdrawal flow rate (minQb). These flow rate boundaries are applied as limits to both the integration term (Item) and the sum of the flow outputs (Qtotal). The maximum withdrawal rate is limited to, e.g., 60 ml/min, to avoid excessive withdrawal flows that might collapse the vein in certain patient populations. The minimum flow rate (minQb) is applied to the output flow to ensure that the pump does not retract at a flow rate higher than −60 ml/min. In addition, if the actual flow rate (Qb) drops below a predetermined rate for a certain period of time, e.g., 20 ml/min for 10 seconds, both the blood pump and ultrafiltrate pump are stopped.

The ultrafiltrate pump is stopped when the blood pump flow is less than 40 ml/min. If the ultrafiltrate pump is not stopped, blood can be condensed too much inside the fibers and the fibers will clot. A minimum shear rate of 1000 sec−1 in blood is desirable if fouling is to be avoided. This shear rate occurs at 40 ml/min in the 0.2 mm diameter filter fibers. The shear rate decreases as the flow rate decreases. Fouling may be due to a buildup of a protein layer on the membrane surface and results in an increase in trans-membrane resistance that can ultimately stop ultrafiltration flow if allowed to continue. By ensuring that no ultrafiltration flow occurs when a low blood shear rate is present, the likelihood of fouling is decreased.

When the system starts blood flow, the ultrafiltration pump is held in position and does not begin rotation until the measured and set blood flow are greater than 40 ml/min. If the set or measured blood flow drops below 40 ml/min, the ultrafiltrate pump is immediately halted. This prevents clogging and fouling. Once blood flow is re-established and is greater than 40 ml/min, the ultrafiltrate pump is restarted at the user defined ultrafiltration rate. When the blood pump is halted the ultrafiltrate pump is stopped first, followed by the blood pump ensuring that the filter does not become clogged because the ultrafiltrate pump was slower at stopping, resulting in ultrafiltrate being entrained while blood flow has ceased. This can be implemented with a 20 millisecond delay between halt commands.

FIG. 6 graphically shows the control algorithms for the blood infusion pressure. The patient may be exposed to excessively high pressures if an occlusion occurs in the infusion vein. Control algorithms are used for controlling the maximum allowable infusion pressure. These algorithms are similar in concept to those for controlling the maximum allowable withdrawal pressure. The maximum occlusion pressure algorithm 601 is a positive relationship between the flow rate (Qb) and infusion pressure (Pin) as measured by the pressure sensor in the return line 110. As shown in the algorithm curve 601, as the flow rate increases the acceptable infusion pressure similarly increases, up to a maximum limit.

The algorithm curve 601 provides the maximum infusion pressure, Pin, for given blood flow. The maximum allowable positive pressure PinOcc increases as blood flow Qb increases. This curve was generated from theoretical and empirical data with a blood Hct of 45% (maximum expected clinically), and is based on the maximum resistance of the infusion tubing 105 and the infusion needle 103. The curve may vary with different embodiments, depending on other data used to generate such a curve.

Figure 7:
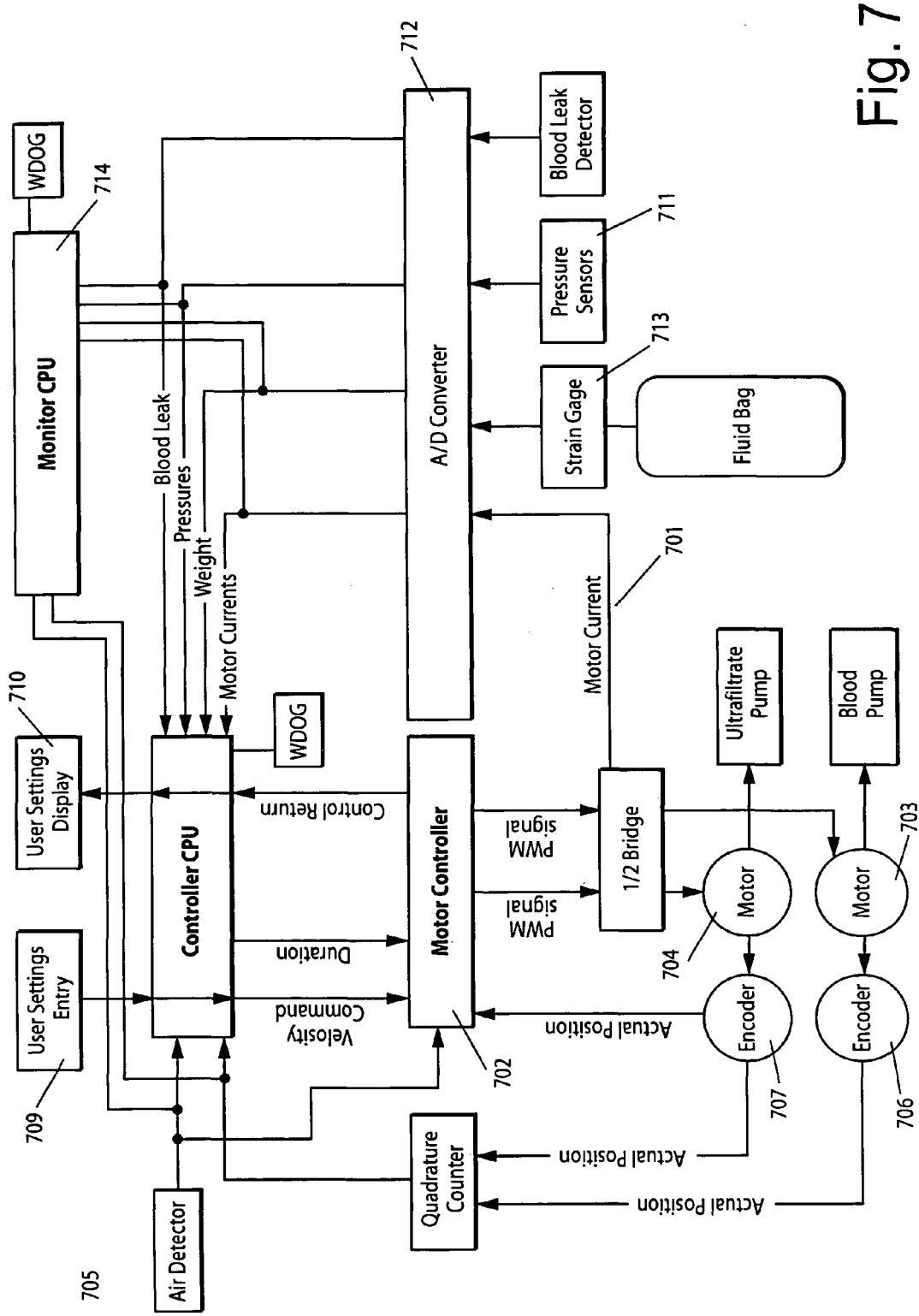
FIG. 7 is a component diagram of the controller (including controller CPU, monitoring CPU and motor CPU), and of the sensor inputs and actuator outputs that interact with the controller.

FIG. 7 illustrates the electrical architecture of the ultrafiltrate system 700 (100 in FIG. 1), showing the various signal inputs and actuator outputs to the controller. The user-operator inputs the desired ultrafiltrate extraction rate into the controller by pressing buttons on a membrane interface keypad 709 on the controller. These settings may include the maximum flow rate of blood through the system, maximum time for running the circuit to filter the blood, the maximum ultrafiltrate rate and the maximum ultrafiltrate volume. The settings input by the user are stored in a memory 715 (mem.), and read and displayed by the controller CPU 705 (central processing unit, e.g., microprocessor or micro-controller) on the display 710.

The controller CPU regulates the pump speeds by commanding a motor controller 702 to set the rotational speed of the blood pump 113 to a certain speed specified by the controller CPU. Similarly, the motor controller adjusts the speed of the ultrafiltrate pump 111 in response to commands from the controller CPU and to provide a particular filtrate flow velocity specified by the controller CPU. Feedback signals from the pressure transducer sensors 711 are converted from analog voltage levels to digital signals in an A/D converter 716. The digital pressure signals are provided to the controller CPU as feedback signals and compared to the intended pressure levels determined by the CPU. In addition, the digital pressure signals may be displayed by the monitor CPU 714.

The motor controller 702 controls the velocity, rotational speed of the blood and filtrate pump motors 703, 704. Encoders 707, 706 mounted to the rotational shaft of each of the motors as feedback provide quadrature signals, e.g., a pair of identical cyclical digital signals, but 90o out-of-phase with one another. These signal pairs are fed to a quadrature counter within the motor controller 702 to give both direction and position. The direction is determined by the signal lead of the quadrature signals. The position of the motor is determined by the accumulation of pulse edges. Actual motor velocity is computed by the motor controller as the rate of change of position. The controller calculates a position trajectory that dictates where the motor must be at a given time and the difference between the actual position and the desired position is used as feedback for the motor controller. The motor controller then modulates the percentage of the on time of the PWM signal sent to the one-half 718 bridge circuit to minimize the error. A separate quadrature counter 717 is independently read by the Controller CPU to ensure that the Motor Controller is correctly controlling the velocity of the motor. This is achieved by differentiating the change in position of the motor over time.

The monitoring CPU 714 provides a safety check that independently monitors each of the critical signals, including signals indicative of blood leaks, pressures in blood circuit, weight of filtrate bag, motor currents, air in blood leak detector 712 and motor speed/position. The monitoring CPU has stored in its memory safety and alarm levels for various operating conditions of the ultrafiltrate system. By comparing these allowable preset levels to the real-time operating signals, the monitoring CPU can determine whether a safety alarm should be issued, and has the ability to independently stop both motors and reset the motor controller and controller CPU if necessary.

Peripheral vein access presents unique problems that make it difficult for a blood withdrawal controller to maintain constant flow and to not create hazards for the patient. For example, a patient may stand up during treatment and thereby increase the static pressure head height on the infusion side of the blood circuit. As the patient rises each centimeter (cm), the measured pressure in the extracorporeal circuit increases by 0.73 mm Hg. This static pressure rise (or fall) will be detected by pressure sensors in the withdrawal tube. The controller adjusts the blood flow rate through the extracorporeal circuit to accommodate for such pressure changes and ensures that the changes do not violate the pressure limits set in the controller.

In addition, the patient may bend their arm during treatment, thereby reducing the blood flow to the withdrawal vein. As the flow through the withdrawal catheter decreases, the controller reduces pump speed to reduce the withdrawal pressure level. Moreover, the blood infusion side of the blood circulation circuit may involve similar pressure variances. These infusion side pressure changes are also monitored by the controller which may adjust the pump flow rate to accommodate such changes.

In some cases, blood flow can be temporarily impeded by the collapse of the withdrawal vein caused by the patient motion. In other cases the withdrawal vein of the patient may not be sufficient to supply the maximum desired flow of 60 ml/min. The software algorithms enable the controller to adjust the withdrawal flow rate of blood to prevent or recover from the collapse of the vein and reestablish the blood flow based on the signal from the withdrawal pressure sensor.

A similar risk of disconnection exists when returning the patient's blood. The infusion needle or the infusion tube between the outlet of the infusion pressure transducer (Pin) and needle may become disconnected during operation. A similar disconnection algorithm (as described for the withdrawal side) is used for detecting the presence of disconnections on the infusion side. In this case an air detector is not used because nursing staff do not place pressure cuffs on the arm being infused because of risk of extravasation. Since the blood is being infused the pressures measured by the infusion pressure transducer Pin are positive. The magnitude of Pin will decrease in the presence of a disconnection due to a decrease in the resistance of the infusion line.

A disconnection is detected when the pressure Pin at a given blood flow is less than the pressure described by curve 602 (FIG. 6) for the same said blood flow. The minimum resistance of the 18 Gage needle and withdrawal tubing, with a blood Hct of 35%, at a temperature of 37° C. are represented by the curve 602. The curve 602, shown in FIG. 6 is described in equation form in 401 (FIG. 4). The infusion disconnection pressure, PinDisc 401 is calculated as a function of blood flow, QbMeas where QbMeas, is actual blood flow calculated from the encoder velocity.

$$PinDisc = QbMeas * KinD + C$$

PinDisc is filtered with a 0.2 Hz low pass filter to avoid false disconnection alarms, reference 401 FIG. 4. The present embodiment uses a linear equation to describe PinDisc, but this equation could also be implemented as a look-up table or a second order polynomial in the presence of turbulent flow. The implementation chosen will be based upon the characteristics of the tube and the presence of laminar or turbulent flow.

$$PinDiscFilt = PinDisc*(1-alpha) + PinDiscFiltOld*alpha$$

$$PinDiscFiltOld = PinDiscFilt$$

If Pin is less than PinDiscFilt for 2 seconds consecutively, an infusion disconnect is declared and the blood pump and ultrafiltrate pump are immediately stopped.

If (Pin>PinDiscFilt)
{Then Increment Infusion Disconnect Timer}
{else Reset Infusion Disconnect Timer}
If (Reset Infusion Disconnect Timer=2 seconds)
{then Declare Infusion Disconnection}

The withdrawal and infusion occlusion detection algorithms use similar methods of detection. Only the specific coefficients describing the maximum and minimum allowable resistances are different.

The purpose of the withdrawal occlusion algorithm is to limit the pressure in the withdrawal vein from becoming negative. A negative pressure in the withdrawal vein will cause it to collapse. The venous pressure is normally 15 mm Hg and it will remain positive as long as the flow in the vein is greater than the flow extracted by the blood pump.

If the resistance of the withdrawal needle and blood circuit tube are known, the withdrawal flow may be controlled by targeting a specific withdrawal pressure as a function of desired flow and known resistance. For example, assume that the resistance of the withdrawal needle to blood flow is R and that R equals −1 mm Hg/ml/min. In order for 60 ml/min of blood to flow through the needle, a pressure drop of 60 mm Hg is required. The pressure may be either positive, pushing blood through the needle or negative, withdrawing blood through the needle. On the withdrawal side of the needle, if a pressure of −60 mm Hg is targeted a blood flow of 60 ml/min will result.

If the flow controller is designed to be based upon resistance, the pressure target required to give the desired flow rate Q would be R*Q. Thus, if a flow of 40 ml/min were required, a pressure of −40 mm Hg would be required as the pressure target. Since the system knows withdrawal flow based upon encoder velocity and is measuring withdrawal pressure, the system is able to measure the actual withdrawal resistance of the needle in real time.

If a maximum resistance limit is placed on the withdrawal needle of −1.1 mm Hg/ml/min, the pressure controller will stop withdrawing flow in the presence of an occlusion. Occlusion can be in the circuit or caused by the vein collapse. The resistance limit is implemented as a maximum pressure allowed for a given flow. Thus, for a resistance limit of −1.1 mm Hg, if the flow drops to 30 ml/min when the current withdrawal pressure is −60 mm Hg in the presence of an occlusion, the maximum pressure allowed is 30 ml/min*−1.1 mm Hg/ml/min=33 mm Hg. This means that the occlusion resistance is −60/30=−2 mm Hg/ml/min. If the occlusion persists when the withdrawal pressure drops to −33 mm Hg, the flow will be reduced to 16.5 ml/min. This will result in a new pressure target of −18.15 mm Hg and so on until the flow stops.

The actual pressure target to deliver the desired flow is difficult to ascertain in advance because of the myriad of variables which effect resistance, blood Hct, needle size within and length within the expected tolerance levels, etc. Instead, the pressure controller targets the maximum resistance allowed, and the flow is limited by the maximum flow output allowed by the pressure controller.

A goal of the control algorithm is to ensure that the pressure at the withdrawal vein never falls below 0 mmHg where vein collapse could occur, or that the infusion pressure exceeds a value that could cause extravasation. If the critical pressure-flow curve is generated at the worst case conditions (highest blood viscosity), the controller will ensure that the pressure in the vein is always above the collapse level or below the extravasation level.

In the fluid path configuration of the blood circuit shown in FIG. 2, there is no pressure transducer at the blood pump outlet and entry to the filter. If a pressure transducer were present, then its signal could also be fed to the PIFF pressure controller using the same pressure limitation methods already described. A specific disconnect and occlusion algorithm could be defined to describe the maximum and minimum flow vs. pressure curves based upon the filter and infusion limb resistance. Alternatively, a limit on the current consumed by the motor can be used to detect the presence of an occlusion in the infusion and filter limb. High pressures at the filter inlet will not be detected by the infusion pressure transducer, (Pin), because it is downstream of this potential occlusion site. A disconnection at the inlet to the filter will be detected by the infusion disconnection algorithm, because if the filter becomes disconnected there will be no flow present in the infusion limb and this will be interpreted by the infusion disconnection algorithm as an infusion disconnection.

The blood pump uses a direct drive brushless DC motor. This design was chosen for long life and efficiency. Using this approach has the added benefit of being able to measure pump torque directly. With DC motors the current consumed is a function of motor velocity and torque. The current consumed by the motor may be measured directly with a series resistor as indicated by 701, FIG. 7. This current is a function of the load torque and back EMF generated by the motor as a function of its speed and voltage constant. Thus:

$$Tmotor = Tpump + Ttube \quad \text{Equation 1}$$

Where Tmotor is the torque required to drive the motor, Tpump is the torque required to overcome the pressure in the tubing, Ttube is the torque required to compress the tube.

$$Tmotor = (Imotor - (RPM*KV)/Rmotor)*KT \quad \text{Equation 2}$$

$$Tmotor = (Imotor - IEMF)*KT \quad \text{Equation 3}$$

Where Tmotor=Torque oz-in, RPM=revs per min of motor, Imotor is the current consumed by the motor, KV is the voltage constant of the motor Volts/rpm, Rmotor=electrical resistance of motor in ohms and KT=the torque constant of the motor in oz-in/amp. KV and KT are constants defined by the motor manufacturer. The RPM of the motor may be calculated from the change in position of the motor encoder. Thus, by measuring the current consumed by the motor, the torque produced by the motor can be calculated if the speed and physical parameters of the motor are known.

The torque consumed by the motor is a function of withdrawal pressure, the blood pump outlet pressure and the tubing compressibility. The torque required to compress the blood circuit tubing is relatively constant and is independent of the blood flow rate. A good indication of the blood pump outlet pressure may be calculated as a function of the current consumed by the blood pump motor and may be used to indicate the presence of a severe occlusion.

The pump Pressure Pp may be expressed as:

$$Tpump = Tmotor - Ttube \quad \text{Equation 4}$$

$$Pp = Tpump * K \quad \text{Equation 5}$$

Where K=A/R $$Pp = (Tmotor - Ttube) * K \quad \text{Equation 6}$$

Where Pp is the blood pump outlet pressure, Tmotor is the total torque output by the motor, Ttube is the torque required to squeeze the blood circuit tube K and is a conversion constant from torque to pressure. K is calculated by dividing the cross-sectional area of the blood circuit tube internal diameter 3.2 mm by the radius R of the peristaltic blood pump.

Since K and Ttube are constants for the system and the blood flow has a range of 40 to 60 ml/min also making the back EMF current approximately constant. The motor current may be used directly without any manipulation to determine the presence of an occlusion as an alternative to calculating Pp. Thus, when the current limit of the blood pump exceeds, for example 3 amps, both the blood pump and the ultrafiltrate pump are stopped.

Figure 8:
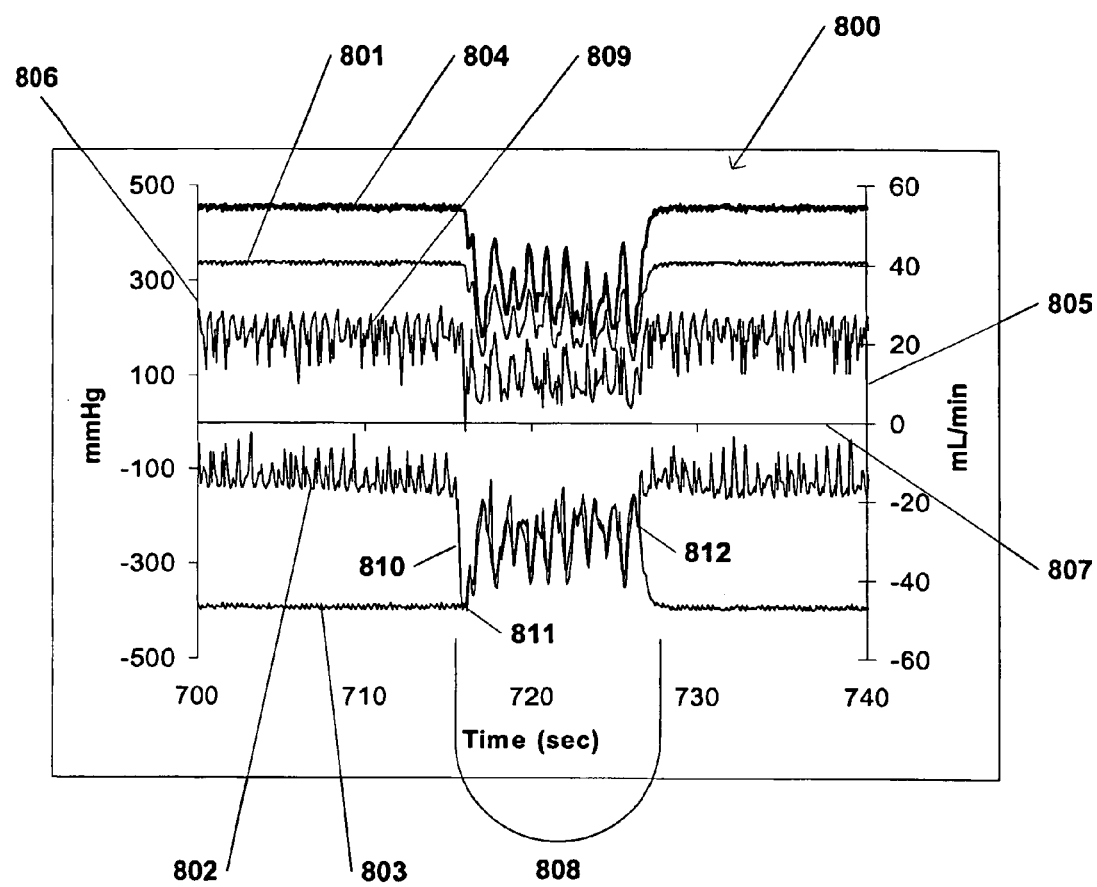
FIG. 8 is an illustration of the system response to the partial occlusion of the withdrawal vein in a patient.

FIG. 8 illustrates the operation of a prototype apparatus constructed according to the current embodiment illustrated by FIGS. 1 to 7 under the conditions of a partial and temporary occlusion of the withdrawal vein. The data depicted in the graph 800 was collected in real time, every 0.1 second, during treatment of a patient. Blood was withdrawn from the left arm and infused into the right arm in different veins of the patient using similar 18 Gage needles. A short segment of data, i.e., 40 seconds long, is plotted in FIG. 8 for the following traces: blood flow in the extracorporeal circuit 804, infusion pressure occlusion limit 801 calculated by CPU 705, infusion pressure 809, calculated withdrawal pressure limit 803 and measured withdrawal pressure 802. Blood flow 804 is plotted on the secondary Y-axis 805 scaled in mL/min. All pressures and pressure limits are plotted on the primary Y-axis 806 scaled in mmHg. All traces are plotted in real time on the X-axis 807 scaled in seconds.

In the beginning, between time marks of 700 and 715 seconds, there is no obstruction in either infusion or withdrawal lines. Blood flow 804 is set by the control algorithm to the maximum flow limit of 55 mL/min. Infusion pressure 809 is approximately 150 to 200 mmHg and oscillates with the pulsations generated by the pump. Infusion occlusion limit 801 is calculated based on the measured blood flow of 55 mmHg and is equal to 340 mmHg. Similarly, the withdrawal pressure 802 oscillates between −100 and −150 mmHg safely above the dynamically calculated withdrawal occlusion limit 803 equal to approximately −390 mmHg.

At approximately 715 seconds, a sudden period of partial occlusion 808 occurred. The occlusion is partial because it did not totally stop the blood flow 804, but rather resulted in its significant reduction from 55 mL/min to between 25 and 44 mL/min. The most probable cause of this partial occlusion is that as the patient moved during blood withdrawal. The partial occlusion occurred at the intake opening of the blood withdrawal needle. Slower reduction in flow can also occur due to a slowing in the metabolic requirements of the patient because of a lack of physical activity. Squeezing a patient's arm occasionally will increase blood flow to the arm, which results in a sudden sharp decrease 810 of the withdrawal pressure 802 from −150 mmHg to −390 mmHg at the occlusion detection event 811. The detection occurred when the withdrawal pressure 810 reached the withdrawal limit 803. The controller CPU responded by switching from the maximum flow control to the occlusion limit control for the duration of the partial occlusion 808. Flow control value was dynamically calculated from the occlusion pressure limit 803. That resulted in the overall reduction of blood flow to 25 to 45 mL/min following changing conditions in the circuit.

FIG. 8 illustrates the occlusion of the withdrawal line only. Although the infusion occlusion limit 801 is reduced in proportion to blood flow 804 during the occlusion period 808, the infusion line is never occluded. This can be determined by observing the occlusion pressure 809 always below the occlusion limit 801 by a significant margin, while the withdrawal occlusion limit 803 and the withdrawal pressure 802 intercept and are virtually equal during the period 808 because the PIFF controller is using the withdrawal occlusion limit 803 as a target.

The rapid response of the control algorithm is illustrated by immediate adjustment of flow in response to pressure change in the circuit. This response is possible due to: (a) servo controlled blood pump equipped with a sophisticated local DSP (digital signal processing) controller with high bandwidth, and (b) extremely low compliance of the blood path. The effectiveness of controls is illustrated by the return of the system to the steady state after the occlusion and or flow reduction disappeared at the point 812. Blood flow was never interrupted, alarm and operator intervention were avoided and the partial occlusion was prevented from escalation into a total occlusion (collapse of the vein) that would have occurred if not for the responsive control based on the withdrawal pressure.

If the system response was not this fast, it is likely that the pump would have continued for some time at the high flow of 55 mL/min. This high flow would have rapidly resulted in total emptying of the vein and caused a much more severe total occlusion. The failure to quickly recover from the total occlusion can result in the treatment time loss, potential alarms emitted from the extracorporeal system, and a potential need to stop treatment altogether, and/or undesired user intervention. Since user intervention can take considerable time, the blood will be stagnant in the circuit for a while. Stagnant blood can be expected to clot over several minutes and make the expensive circuit unusable for further treatment.

Figure 9:
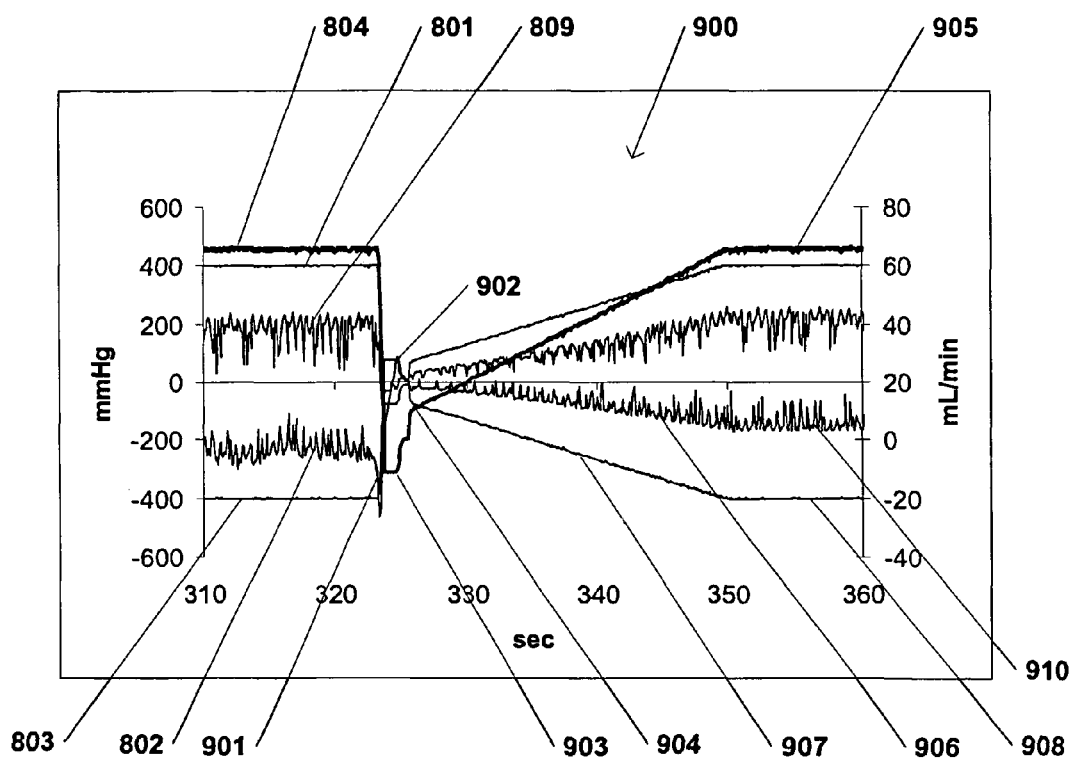
FIG. 9 is an illustration of the system response to the complete occlusion and temporary collapse of the withdrawal vein in a patient.

FIG. 9 illustrates a total occlusion of the blood withdrawal vein access in a different patient, but using the same apparatus as used to obtain the data shown in FIG. 8. Traces on the graph 900 are similar to those on the graph 800. The primary Y-axis (months) and secondary Y-axis (mL/min) correspond to pressure and flow, respectively, in the blood circuit. The X-axis is time in seconds. As in FIG. 8 the system is in steady state at the beginning of the graph. The blood flow 804 is controlled by the maximum flow algorithm and is equal to 66 mL/min. The withdrawal pressure 802 is at average of −250 mmHg and safely above the occlusion limit 803 at 400 mmHg until the occlusion event 901. Infusion pressure 809 is at average of 190 mmHg and way below the infusion occlusion limit 801 that is equal to 400 mmHg.

As depicted in FIG. 9, the occlusion of the withdrawal access is abrupt and total. The withdrawal vein has likely collapsed due to the vacuum generated by the needle or the needle opening could have sucked in the wall of the vein. The withdrawal vein is completely closed. Similar to the partial occlusion illustrated by FIG. 8, the rapid reduction of the blood flow 804 by the control system in response to the decreasing (more negative) withdrawal pressure 802 prevented escalation of the occlusion, but resulted in crossing of the occlusion limit 803 into positive values at the point 902. Simultaneously the blood flow 804 dropped to zero and sequentially became negative (reversed direction) for a short duration of time 903. The control system allowed reversed flow continued for 1 second at 10 mL/min as programmed into an algorithm. This resulted in possible re-infusion of 0.16 mL of blood back into the withdrawal vein. These parameters were set for the experiment and may not reflect an optimal combination. The objective of this maneuver is to release the vein wall if it was sucked against the needle orifice. It also facilitated the refilling of the vein if it was collapsed.

During the short period of time when the blood flow in the circuit was reversed, occlusion limits and algorithms in both infusion and withdrawal limbs of the circuit remained active. The polarity of the limits was reversed in response to the reversed direction of flow and corresponding pressure gradients.

The success of the maneuver is illustrated by the following recovery from total occlusion. At the point 904 signifying the end of allowed flow reversal, the withdrawal occlusion limit 803 became negative and the infusion occlusion limit 801 became positive again. The blood pump started the flow increase ramp shown between points 904 and 905. The gradual ramp at a maximum allowed rate is included in the total occlusion recovery algorithm to prevent immediate re-occlusion and to allow the withdrawal vein to refill with blood.

For the example illustrated by FIG. 9, the most likely cause of the occlusion was suction of the blood vessel wall to the withdrawal needle intake opening. The occlusion onset was rapid and the condition disappeared completely after the short reversal of flow that allowed the vessel to re-inflate. It can be observed that while the withdrawal occlusion ramp 907 followed the blood flow ramp 905, the measured withdrawal pressure 906 did not anymore intercept it. In fact, by the time the steady-state condition was restored, the withdrawal pressure 910 was at approximately −160 mmHg. Prior to occlusion the withdrawal pressure level 802 was approximately −200 mmHg. Thus, the withdrawal conditions have improved as a result of the total occlusion maneuver.

The preferred embodiment of the invention now known to the invention has been fully described here in sufficient detail such that one of ordinary skill in the art is able to make and use the invention using no more than routine experimentation. The embodiments disclosed herein are not all of the possible embodiments of the invention. Other embodiments of the invention that are within the sprite and scope of the claims are also covered by this patent.

What is claimed is:

1. A method to control blood flow in an extracorporeal blood system that withdraws blood from a vascular system of a patient, said method comprising:
   a. withdrawing blood from the vascular system into the extracorporeal blood system;
   b. determining a withdrawal pressure of the withdrawn blood in the extracorporeal blood system;
   c. comparing the withdrawal pressure to a withdrawal pressure target;
   d. adjusting the flow rate if the withdrawal pressure is less than a withdrawal pressure target;
   e. temporarily ceasing the flow if the adjusted flow rate becomes less than a predefined flow rate limit, and
   f. automatically restarting the flow after the temporary cessation.

2. The method in claim 1 wherein the blood is withdrawn at a predefined maximum flow rate prior to adjusting the flow rate.

3. The method in claim 1 further comprising:
   g. infusing the withdrawn blood from the system into the vascular system simultaneous with the withdrawal of blood from the vascular system;
   h. determining an infusion pressure of the blood being infused, and
   i. adjusting the flow rate if the infusion pressure is greater than the infusion pressure target.

4. The method in claim 3 further comprising:
   j. switching control of the flow rate adjustment from adjusting due to the withdrawal pressure being less than the withdrawal target to adjusting due to the infusion pressure being greater than the infusion pressure, and
   k. applying substantially the same adjusted flow rate last used to control withdrawal pressure as the adjusted flow rate to begin control infusion pressure.

5. The method in claim 3 wherein the flow rate is at a predetermined maximum flow rate if the withdrawal pressure is above the withdrawal pressure target and the infusion pressure is below the infusion pressure target.

6. The method in claim 3 wherein the flow rate adjustment is a gradual reduction in flow rate.

7. The method in claim 5 wherein the predetermined maximum flow rate is set by a user of the extracorporeal blood system.

8. A system for controlling blood flow withdrawn from and infused back into a patient comprising:
   an extracorporeal circuit having a blood passage including a blood withdrawal tube, a blood treatment device and an infusion tube;
   a withdrawal pressure sensor sensing a blood pressure in the withdrawal tube and an infusion pressure sensor sensing a blood pressure in the infusion tube;
   a pump coupled to the circuit and adapted to move blood through the circuit at a controlled flow rate, and
   a pump controller receiving blood pressure signals from the withdrawal and infusion pressure sensors and using the pressure signals to control the pump to regulate the controlled flow rate, wherein the pump controller includes a processor and a memory storing a control algorithm of a withdrawal pressure target and an infusion pressure target, said controller reduces the controlled flow rate based on a difference between a withdrawal pressure sensed by the withdrawal pressure sensor and the withdrawal pressure target and based on a difference between an infusion pressure sensed by the infusion pressure sensor and the infusion pressure target.

9. The system of claim 8 wherein the control algorithm includes a predetermined maximum flow rate applied as the controlled flow rate when the withdrawal pressure is above the withdrawal pressure target and the infusion pressure is below the infusion pressure target.

10. The system of claim 9 wherein the predetermined maximum flow rate is selected by a user of the system.

11. The system of claim 8 wherein the withdrawal tube is connectable to a blood vessel.

12. The system of claim 8 wherein the infusion tube is connectable to a blood vessel.

13. The system of claim 8 wherein the pump controller includes a closed loop pressure controller with a predefined maximum flow rate.

14. The system of claim 13 wherein the predefined maximum flow rate is selected by a user of the system.

15. The system of claim 8 wherein the withdrawal pressure target varies with blood flow rate.

16. The system of claim 8 wherein the infusion pressure target varies with blood flow rate.

17. The system of claim 13 whereby the pump ceases flow for a duration of time when the flow rate is controlled below a percentage of the predefined maximum flow rate.

18. The system of claim 13 wherein the controller reverses the pump and thereby reverses the flow in the circuit if the controlled flow rate is reduced to below a predefined percentage of the predefined maximum flow rate.

19. The system of claim 8 wherein the controller reverses the pump and thereby reverses the flow in the circuit if the controlled flow rate is reduced to below a predefined condition stored in the controller, and further the withdrawal pressure target and infusion pressure target are inverted while flow is reversed.

20. A method to control blood flow in an extracorporeal blood system that withdraws blood from a vascular system of a patient, wherein said extracorporeal blood system includes a blood passage, pump coupled to the blood passage and a controller, said method comprising:
reducing a pressure in the blood passage by the pump applying a pumping action to the blood passage, wherein the pumping action of the pump is controlled by the controller;
withdrawing blood from the vascular system into the blood passage due to the reduced pressure in the blood passage;
sensing a withdrawal pressure of the withdrawn blood in the blood passage and providing the sensed withdrawal pressure to the controller;
comparing the withdrawal pressure to a withdrawal pressure target, wherein the comparison is performed automatically by the controller;
adjusting the flow rate if the withdrawal pressure is less than a withdrawal pressure target, wherein the adjustment is determined by the controller which effects a change to the pumping action;
temporarily ceasing the flow if the adjusted flow rate becomes less than a predefined flow rate limit, wherein the temporary cessation of the flow is caused by the controller temporarily stopping the pumping action, and
automatically restarting the flow after the temporary cessation, wherein the automatic restart of the flow is caused by the controller restarting the pumping action of the pump.

21. The method in claim 20 wherein the blood is withdrawn at a predefined maximum flow rate prior to adjusting the flow rate.

22. The method in claim 20 further comprising:
treating the withdrawn blood flowing through the blood passage in the extracorporeal blood system;
infusing the treated blood from the blood passage to the vascular system simultaneous with the withdrawal of blood from the vascular system;
sensing an infusion pressure of the blood being infused and providing the infusion pressure to the controller, and
adjusting the flow rate if the infusion pressure is greater than the infusion pressure target, wherein the adjustment of the flow rate is determined by the controller and.

23. The method in claim 22 further comprising:
the controller switching control of the flow rate adjustment from adjusting due to the withdrawal pressure being less than the withdrawal target to adjusting due to the infusion pressure being greater than the infusion pressure, and
the controller applying substantially the same adjusted flow rate last used to control withdrawal pressure as the adjusted flow rate to begin control infusion pressure.

24. The method in claim 22 wherein the controller sets the flow rate at a predetermined maximum flow rate if the withdrawal pressure is above the withdrawal pressure target and the infusion pressure is below the infusion pressure target.

25. The method in claim 22 wherein the flow rate adjustment is a gradual reduction in flow rate determined by the controller.

* * * * *